US009009958B2

(12) United States Patent  
Etzkorn

(10) Patent No.: US 9,009,958 B2
(45) Date of Patent: Apr. 21, 2015

(54) SYSTEMS AND METHODS FOR ENCAPSULATING ELECTRONICS IN A MOUNTABLE DEVICE

(71) Applicant: Google Inc., Mountain View, CA (US)

(72) Inventor: James Etzkorn, Mountain View, CA (US)

(73) Assignee: Google Inc., Mountain View, CA (US)

( * ) Notice: Subject to any disclaimer, the term of this patent is extended or adjusted under 35 U.S.C. 154(b) by 0 days.

(21) Appl. No.: 14/034,303

(22) Filed: Sep. 23, 2013

(65) Prior Publication Data

US 2014/0296674 A1    Oct. 2, 2014

Related U.S. Application Data

(63) Continuation of application No. 13/851,290, filed on Mar. 27, 2013.

(51) Int. Cl.
H05K 3/30 (2006.01)
A61B 5/145 (2006.01)
(Continued)

(52) U.S. Cl.
CPC ........ A61B 5/14546 (2013.01); G01N 27/3272 (2013.01); C12Q 1/006 (2013.01);
(Continued)

(58) Field of Classification Search
CPC .......... G01N 27/3272; A61B 5/14532; A61B 5/14546; C12Q 1/006; G02B 1/043; G02C 7/049
USPC ............ 29/832, 841, 846, 848, 851; 600/319, 600/345, 347, 365
See application file for complete search history.

(56) References Cited

U.S. PATENT DOCUMENTS 3,958,560 A    5/1976  March
4,014,321 A    3/1977  March
(Continued)

FOREIGN PATENT DOCUMENTS

EP    0369942    5/1990
EP    0686372    12/1995
(Continued)

OTHER PUBLICATIONS

Badugu et al., "A Glucose Sensing Contact Lens: A Non-Invasive Technique for Continuous Physiological Glucose Monitoring," Journal of Fluorescence, Sep. 2003, pp. 371-374, vol. 13, No. 5.
(Continued)

Primary Examiner — Peter DungBa Vo
Assistant Examiner — Jeffrey T Carley
(74) Attorney, Agent, or Firm — McDonnell Boehnen Hulbert & Berghoff LLP

(57) ABSTRACT

A mountable device includes a bio-compatible structure embedded in a polymer that defines at least one mounting surface. The bio-compatible structure includes an electronic component having electrical contacts, sensor electrodes, and electrical interconnects between the sensor electrodes and the electrical contacts. The bio-compatible structure is fabricated such that it is fully encapsulated by a bio-compatible material, except for the sensor electrodes. In the fabrication, the electronic component is positioned on a first layer of bio-compatible material and a second layer of bio-compatible material is formed over the first layer of bio-compatible material and the electronic component. The electrical contacts are exposed by removing a portion of the second layer, a conductive pattern is formed to define the sensor electrodes and electrical interconnects, and a third layer of bio-compatible material is formed over the conductive pattern. The sensor electrodes are exposed by removing a portion of the third layer.

15 Claims, 10 Drawing Sheets

(51) Int. Cl.

| | |
|---|---|
| *G01N 27/327* | (2006.01) |
| *C12Q 1/00* | (2006.01) |
| *G02B 1/04* | (2006.01) |
| *G02C 7/04* | (2006.01) |
| *A61B 5/1473* | (2006.01) |
| *A61B 5/00* | (2006.01) |
| *H05K 3/32* | (2006.01) |
| *H05K 1/18* | (2006.01) |
| *A61B 5/1477* | (2006.01) |

(52) U.S. Cl.
CPC ............ *G02B 1/043* (2013.01); *G02C 7/049* (2013.01); *A61B 5/1473* (2013.01); *A61B 5/6813* (2013.01); *H05K 3/32* (2013.01); *H05K 1/185* (2013.01); *H05K 2201/10098* (2013.01); *H05K 2201/10151* (2013.01); *H05K 2203/1469* (2013.01); *A61B 5/1477* (2013.01); *A61B 5/6821* (2013.01); *G02C 7/04* (2013.01); *A61B 2560/0214* (2013.01); *A61B 2562/12* (2013.01)

(56) References Cited

U.S. PATENT DOCUMENTS

| | | | |
|---|---|---|---|
| 4,055,378 A | 10/1977 | Feneberg et al. | |
| 4,122,942 A | 10/1978 | Wolfson | |
| 4,136,250 A | 1/1979 | Mueller et al. | |
| 4,143,949 A | 3/1979 | Chen | |
| 4,153,641 A | 5/1979 | Deichert et al. | |
| 4,214,014 A | 7/1980 | Hofer et al. | |
| 4,309,085 A | 1/1982 | Morrison | |
| 4,312,575 A | 1/1982 | Peyman et al. | |
| 4,401,371 A | 8/1983 | Neefe | |
| 4,463,149 A | 7/1984 | Ellis | |
| 4,555,372 A | 11/1985 | Kunzler et al. | |
| 4,604,479 A | 8/1986 | Ellis | |
| 4,632,844 A | 12/1986 | Yanagihara et al. | |
| 4,686,267 A | 8/1987 | Ellis et al. | |
| 4,740,533 A | 4/1988 | Su et al. | |
| 4,826,936 A | 5/1989 | Ellis | |
| 4,996,275 A | 2/1991 | Ellis et al. | |
| 4,997,770 A | 3/1991 | Giles et al. | |
| 5,032,658 A | 7/1991 | Baron et al. | |
| 5,034,461 A | 7/1991 | Lai et al. | |
| 5,070,215 A | 12/1991 | Bambury et al. | |
| 5,135,297 A | 8/1992 | Valint et al. | |
| 5,177,165 A | 1/1993 | Valint et al. | |
| 5,177,168 A | 1/1993 | Baron et al. | |
| 5,219,965 A | 6/1993 | Valint et al. | |
| 5,260,000 A | 11/1993 | Nandu et al. | |
| 5,271,875 A | 12/1993 | Appleton et al. | |
| 5,310,779 A | 5/1994 | Lai | |
| 5,321,108 A | 6/1994 | Kunzler et al. | |
| 5,326,584 A | 7/1994 | Kamel et al. | |
| 5,336,797 A | 8/1994 | McGee et al. | |
| 5,346,976 A | 9/1994 | Ellis et al. | |
| 5,358,995 A | 10/1994 | Lai et al. | |
| 5,364,918 A | 11/1994 | Valint et al. | |
| 5,387,662 A | 2/1995 | Kunzler et al. | |
| 5,449,729 A | 9/1995 | Lai | |
| 5,472,436 A | 12/1995 | Fremstad | |
| 5,512,205 A | 4/1996 | Lai | |
| 5,585,871 A | 12/1996 | Linden | |
| 5,610,252 A | 3/1997 | Bambury et al. | |
| 5,616,757 A | 4/1997 | Bambury et al. | |
| 5,682,210 A | 10/1997 | Weirich | |
| 5,708,094 A | 1/1998 | Lai et al. | |
| 5,710,302 A | 1/1998 | Kunzler et al. | |
| 5,714,557 A | 2/1998 | Kunzler et al. | |
| 5,726,733 A | 3/1998 | Lai et al. | |
| 5,760,100 A | 6/1998 | Nicholson et al. | |
| 5,908,906 A | 6/1999 | Kunzler et al. | |
| 5,981,669 A | 11/1999 | Valint et al. | |
| 6,087,941 A | 7/2000 | Ferraz et al. | |
| 6,131,580 A | 10/2000 | Ratner et al. | |
| 6,193,369 B1 | 2/2001 | Valint et al. | |
| 6,200,626 B1 | 3/2001 | Grobe et al. | |
| 6,213,604 B1 | 4/2001 | Valint et al. | |
| 6,312,393 B1 | 11/2001 | Abreu | |
| 6,348,507 B1 | 2/2002 | Heiler et al. | |
| 6,366,794 B1 | 4/2002 | Moussy et al. | |
| 6,423,001 B1 | 7/2002 | Abreu | |
| 6,428,839 B1 | 8/2002 | Kunzler et al. | |
| 6,431,705 B1 | 8/2002 | Linden | |
| 6,440,571 B1 | 8/2002 | Valint et al. | |
| 6,450,642 B1 | 9/2002 | Jethmalani et al. | |
| 6,532,298 B1 | 3/2003 | Cambier et al. | |
| 6,544,193 B2 | 4/2003 | Abreu | |
| 6,550,915 B1 | 4/2003 | Grobe, III | |
| 6,570,386 B2 | 5/2003 | Goldstein | |
| 6,579,235 B1 | 6/2003 | Abita et al. | |
| 6,599,559 B1 | 7/2003 | McGee et al. | |
| 6,614,408 B1 | 9/2003 | Mann | |
| 6,630,243 B2 | 10/2003 | Valint et al. | |
| 6,638,563 B2 | 10/2003 | McGee et al. | |
| 6,726,322 B2 | 4/2004 | Andino et al. | |
| 6,735,328 B1 | 5/2004 | Helbing et al. | |
| 6,779,888 B2 | 8/2004 | Marmo | |
| 6,804,560 B2 | 10/2004 | Nisch et al. | |
| 6,851,805 B2 | 2/2005 | Blum et al. | |
| 6,885,818 B2 | 4/2005 | Goldstein | |
| 6,939,299 B1 | 9/2005 | Petersen et al. | |
| 6,980,842 B2 | 12/2005 | March et al. | |
| 7,018,040 B2 | 3/2006 | Blum et al. | |
| 7,131,945 B2 | 11/2006 | Fink et al. | |
| 7,169,106 B2 | 1/2007 | Fleischman et al. | |
| 7,398,119 B2 | 7/2008 | Lambert et al. | |
| 7,423,801 B2 | 9/2008 | Kaufman et al. | |
| 7,429,465 B2 | 9/2008 | Muller et al. | |
| 7,441,892 B2 | 10/2008 | Hsu | |
| 7,443,016 B2 | 10/2008 | Tsai et al. | |
| 7,450,981 B2 | 11/2008 | Jeon | |
| 7,639,845 B2 | 12/2009 | Utsunomiya | |
| 7,654,671 B2 | 2/2010 | Glynn | |
| 7,699,465 B2 | 4/2010 | Dootjes et al. | |
| 7,728,949 B2 | 6/2010 | Clarke et al. | |
| 7,751,896 B2 | 7/2010 | Graf et al. | |
| 7,774,931 B2 | 8/2010 | Tai et al. | |
| 7,799,243 B2 | 9/2010 | Mather et al. | |
| 7,809,417 B2 | 10/2010 | Abreu | |
| 7,810,233 B2 | 10/2010 | Krulevitch et al. | |
| 7,878,650 B2 | 2/2011 | Fritsch et al. | |
| 7,885,698 B2 | 2/2011 | Feldman | |
| 7,907,931 B2 | 3/2011 | Hartigan et al. | |
| 7,926,940 B2 | 4/2011 | Blum et al. | |
| 7,931,832 B2 | 4/2011 | Pugh et al. | |
| 7,964,390 B2 | 6/2011 | Rozakis et al. | |
| 8,048,628 B2 | 11/2011 | Pollack et al. | |
| 8,080,187 B2 | 12/2011 | Tepedino, Jr. et al. | |
| 8,096,654 B2 | 1/2012 | Amirparviz et al. | |
| 8,118,752 B2 | 2/2012 | Hetling et al. | |
| 8,142,016 B2 | 3/2012 | Legerton et al. | |
| 8,145,322 B1 | 3/2012 | Yao et al. | |
| 8,224,415 B2 | 7/2012 | Budiman | |
| 2002/0126459 A1* | 9/2002 | Albert et al. .................. 361/743 |
| 2002/0193674 A1 | 12/2002 | Fleischman et al. | |
| 2003/0179094 A1 | 9/2003 | Abreu | |
| 2004/0027536 A1 | 2/2004 | Blum et al. | |
| 2004/0116794 A1 | 6/2004 | Fink et al. | |
| 2005/0045589 A1 | 3/2005 | Rastogi et al. | |
| 2005/0221276 A1 | 10/2005 | Rozakis et al. | |
| 2007/0016074 A1 | 1/2007 | Abreu | |
| 2007/0030443 A1 | 2/2007 | Chapoy et al. | |
| 2007/0121065 A1 | 5/2007 | Cox et al. | |
| 2007/0188710 A1 | 8/2007 | Hetling et al. | |
| 2008/0208335 A1 | 8/2008 | Blum et al. | |
| 2008/0218696 A1 | 9/2008 | Mir | |
| 2009/0033863 A1 | 2/2009 | Blum et al. | |
| 2009/0036761 A1 | 2/2009 | Abreu | |
| 2009/0057164 A1 | 3/2009 | Minick et al. | |
| 2009/0076367 A1 | 3/2009 | Sit et al. | |
| 2009/0118604 A1 | 5/2009 | Phan et al. | |
| 2009/0189830 A1 | 7/2009 | Deering et al. | |
| 2009/0196460 A1 | 8/2009 | Jakobs et al. | |

(56) References Cited

U.S. PATENT DOCUMENTS

| | | | |
|---|---|---|---|
| 2010/0001926 | A1 | 1/2010 | Amirparviz et al. |
| 2010/0013114 | A1 | 1/2010 | Bowers et al. |
| 2010/0016704 | A1 | 1/2010 | Naber et al. |
| 2010/0028559 | A1 | 2/2010 | Yan et al. |
| 2010/0072643 | A1 | 3/2010 | Pugh et al. |
| 2010/0103368 | A1 | 4/2010 | Amirparviz et al. |
| 2010/0109175 | A1 | 5/2010 | Pugh et al. |
| 2010/0110372 | A1 | 5/2010 | Pugh et al. |
| 2010/0113901 | A1 | 5/2010 | Zhang et al. |
| 2010/0133510 | A1 | 6/2010 | Kim et al. |
| 2010/0145422 | A1 | 6/2010 | Seymour et al. |
| 2010/0249548 | A1 | 9/2010 | Muller |
| 2011/0015512 | A1 | 1/2011 | Pan et al. |
| 2011/0028807 | A1 | 2/2011 | Abreu |
| 2011/0040161 | A1 | 2/2011 | Abreu |
| 2011/0055317 | A1 | 3/2011 | Vonog et al. |
| 2011/0063568 | A1 | 3/2011 | Meng et al. |
| 2011/0084834 | A1 | 4/2011 | Sabeta |
| 2011/0116035 | A1 | 5/2011 | Fritsch et al. |
| 2011/0157541 | A1 | 6/2011 | Peyman |
| 2011/0157544 | A1 | 6/2011 | Pugh et al. |
| 2011/0184271 | A1 | 7/2011 | Veciana et al. |
| 2011/0274680 | A1 | 11/2011 | Mazed et al. |
| 2011/0286064 | A1 | 11/2011 | Burles et al. |
| 2011/0298794 | A1 | 12/2011 | Freedman |
| 2012/0026458 | A1 | 2/2012 | Qiu et al. |
| 2012/0038881 | A1 | 2/2012 | Amirparviz et al. |
| 2012/0041287 | A1 | 2/2012 | Goodall et al. |
| 2012/0041552 | A1 | 2/2012 | Chuck et al. |
| 2012/0069254 | A1 | 3/2012 | Burton |
| 2012/0075168 | A1 | 3/2012 | Osterhout et al. |
| 2012/0075574 | A1 | 3/2012 | Pugh et al. |
| 2012/0078071 | A1 | 3/2012 | Bohm et al. |
| 2012/0088258 | A1 | 4/2012 | Bishop et al. |
| 2012/0092612 | A1 | 4/2012 | Binder |
| 2012/0109296 | A1 | 5/2012 | Fan |
| 2012/0177576 | A1 | 7/2012 | Hu |
| 2012/0201755 | A1 | 8/2012 | Rozakis et al. |
| 2012/0218508 | A1 | 8/2012 | Pugh et al. |
| 2012/0239125 | A1 | 9/2012 | Greenberg et al. |
| 2012/0245444 | A1* | 9/2012 | Otis et al. ............ 600/345 |
| 2012/0259188 | A1 | 10/2012 | Besling |
| 2012/0302861 | A1 | 11/2012 | Marshall et al. |

FOREIGN PATENT DOCUMENTS

| | | |
|---|---|---|
| EP | 1061874 | 12/2000 |
| EP | 1818008 | 8/2007 |
| EP | 1947501 | 7/2008 |
| EP | 1617757 | 8/2009 |
| EP | 2457122 | 5/2012 |
| WO | 95/04609 | 2/1995 |
| WO | 01/16641 | 3/2001 |
| WO | 01/34312 | 5/2001 |
| WO | 03/065876 | 8/2003 |
| WO | 03090611 A1 | 11/2003 |
| WO | 2004/060431 | 7/2004 |
| WO | 2004/064629 | 8/2004 |
| WO | 2006/015315 | 2/2006 |
| WO | 2009/094643 | 7/2009 |
| WO | 2010/105728 | 9/2010 |
| WO | 2010/133317 | 11/2010 |
| WO | 2011/011344 | 1/2011 |
| WO | 2011/034592 | 3/2011 |
| WO | 2011/035228 | 3/2011 |
| WO | 2011/035262 | 3/2011 |
| WO | 2011039062 A1 | 4/2011 |
| WO | 2011/083105 | 7/2011 |
| WO | 2011/163080 | 12/2011 |
| WO | 2012/035429 | 3/2012 |
| WO | 2012/037455 | 3/2012 |
| WO | 2012/051167 | 4/2012 |
| WO | 2012/051223 | 4/2012 |
| WO | 2012052765 | 4/2012 |

OTHER PUBLICATIONS

Carlson et al., "A 20 mV Input Boost Converter With Efficient Digital Control for Thermoelectric Energy Harvesting," IEEE Journal of Solid-State Circuits, Apr. 2010, pp. 741-750, vol. 45, No. 4.

Chu et al., "Biomedical soft contact-lens sensor for in situ ocular biomonitoring of tear contents," Biomed Microdevices, 2011, pp. 603-611, vol. 13.

Chu et al., "Soft contact lens biosensor for in situ monitoring of tear glucose as non-invasive blood sugar assessment," Talanta, 2011, pp. 960-965, vol. 83.

Ho et al., "Contact Lens With Integrated Inorganic Semiconductor Devices," MEMS 2008. IEEE 21st International Conference on. IEEE, 2008., pp. 403-406.

Lähdesmäki et al., "Possibilities for Continuous Glucose Monitoring by a Functional Contact Lens," IEEE Instrumentation & Measurement Magazine, Jun. 2010, pp. 14-17.

Lingley et al., "A contact lens with integrated micro solar cells," Microsyst Technol, 2012, pp. 453-458, vol. 18.

Parviz, Babak A., "For Your Eyes Only," IEEE Spectrum, Sep. 2009, pp. 36-41.

Saeedi, E. et al., "Self-assembled crystalline semiconductor optoelectronics on glass and plastic," J. Micromech. Microeng., 2008, pp. 1-7, vol. 18.

Saeedi et al., "Self-Assembled Inorganic Micro-Display on Plastic," Micro Electro Mechanical Systems, 2007. MEMS. IEEE 20th International Conference on. IEEE, 2007., pp. 755-758.

Sensimed Triggerfish, Sensimed Brochure, 2010, 10 pages.

Shih, Yi-Chun et al., "An Inductorless DC-DC Converter for Energy Harvesting With a 1.2-μW Bandgap-Referenced Output Controller," IEEE Transactions on Circuits and Systems-II: Express Briefs, Dec. 2011, pp. 832-836, vol. 58, No. 12.

Shum et al., "Functional modular contact lens," Proc. of SPIE, 2009, pp. 73970K-1 to 73970K-8, vol. 7397.

Stauth et al., "Self-assembled single-crystal silicon circuits on plastic," PNAS, Sep. 19, 2006, pp. 13922-13927, vol. 103, No. 38.

Yao, H. et al., "A contact lens with integrated telecommunication circuit and sensors for wireless and continuous tear glucose monitoring," J. Micromech. Microeng., 2012, pp. 1-10, vol. 22.

Yao, H. et al., "A Dual Microscal Glucose Sensor on a Contact Lens, Tested in Conditions Mimicking the Eye," Micro Electro Mechanical Systems (MEMS), 2011 IEEE 24th International Conference on. IEEE, 2011, pp. 25-28.

Yao et al., "A contact lens with embedded sensor for monitoring tear glucose level," Biosensors and Bioelectronics, 2011, pp. 3290-3296, vol. 26.

Yao, H. et al., "A Soft Hydrogel Contact Lens with an Encapsulated Sensor for Tear Glucose Monitoring," Micro Electro Mechanical Systems (MEMS), 2012 IEEE 25th International Conference on. IEEE, 2012, pp. 769-772.

Yeager et al., "A 9 μA, Addressable Gen2 Sensor Tag for Biosignal Acquistion," IEEE Journal of Solid-State Circuits, Oct. 2010, pp. 2198-2209, vol. 45, No. 10.

Zhang et al., "Design for Ultra-Low Power Biopotential Amplifiers for Biosignal Acquistion Applications," IEEE Transactions on Biomedical Circuits and Systems, 2012, pp. 344-355, vol. 6, No. 4.

Bionic contact lens 'to project emails before eyes,' http://www.kurzweilai.netforums/topic/bionic-contact-lens-to-project-emails-before-eyes, Last accessed Mar. 14, 2012, 2 pages.

Brahim, et al., "Polypyrrole-hydrogel composites for the construction of clinically important biosensors," 2002, Biosensors & Bioelectronics, pp. 53-59, vol. 17.

Chen, et al., "Microfabricated Implantable Parylene-Based Wireless Passive Intraocular Pressure Sensors," Journal of Microelectromechanical Systems, Dec. 2008, pp. 1342-1351, vol. 17, No. 6.

Chu, et al., "Soft Contact-lens Sensor for Monitoring Tear Sugar as Novel Wearable Device of Body Sensor Network," http://www.ksi edu/seke/dms11/DMS/2_Kohji_Mitsubayashi.pdf, Last accessed Jul. 27, 2012, 4 pages.

(56) References Cited

OTHER PUBLICATIONS

"Contact Lenses: Look Into My Eyes," The Economist, Jun. 2, 2011, http://www.economist.com/node/18750624/print, Last accessed Mar. 13, 2012, 8 pages.

Haders, "New Controlled Release Technologies Broaden Opportunities for Ophthalmic Therapies," Drug Delivery Technology, Jul./Aug. 2009, pp. 48-53, vol. 8, No. 7.

Holloway, "Microsoft developing electronic contact lens to monitor blood sugar," Gizmag, Jan. 5, 2012, http://www.gizmag.com/microsoft-electronic-diabetic-contact-lens/20987/, Last accessed Mar. 13, 2012. 5 pages.

Huang, et al., "Wrinkling of Ultrathin Polymer Films," Mater. Res. Soc. Symp. Proc., 2006, 6 pages, vol. 924, Materials Research Society.

Hurst, "How contact lenses could help save your life," Mail Online, Apr. 19, 2010, http://www.dailymail.co.uk/health/article-1267345/How-contact-lenses-help-save-life.html, Last accessed Jul. 27, 2012.

Liao, et al., "A 3-µW CMOS Glucose Sensor for Wireless Contact-Lens Tear Glucose Monitoring," IEEE Journal of Solid-State Circuits, Jan. 2012, pp. 335-344, vol. 47, No. 1.

Liao, et al., "A 3-µW Wirelessly Powered CMOS Glucose Sensor for an Active Contact Lens," 2011 IEEE International Solid-State Circuits Conference, Session 2, Feb. 21, 2011, 3 pages.

Lingley, et al., "A Single-Pixel Wireless Contact Lens Display," Journal of Micromechanics and Microengineering, 2011, pp. 1-8.

Lingley, et al., "Multipurpose integrated active contact lenses," SPIE, 2009, 2 pages.

Liu, et al., "Miniature Amperometric Self-Powered Continuous Glucose Sensor with Linear Response," Analytical Chemistry, 2012, 7 pages.

Loncar, et al., "Design and Fabrication of Silicon Photonic Crystal Optical Waveguides," Journal of Lightwave Technology, Oct. 2000, pp. 1402-1411, vol. 18, No. 10.

Murdan, "Electro-responsive drug delivery from hydrogels," Journal of Controlled Release, 2003, pp. 1-17, vol. 92.

Pandey, et al., "A Fully Integrated RF-Powered Contact Lens With a Single Element Display," IEEE Transactions on Biomedical Circuits and Systems, Dec. 2010, pp. 454-461, vol. 4, No. 6.

Parviz, Babak A., "Augmented Reality in a Contact Lens," IEEE Spectrum, Sep. 2009, http://spectrum.ieee.org/biomedical/bionics/augmented-reality-in-a-contact-lens/0, Last accessed Mar. 14, 2012, 6 pages.

Selner, et al., "Novel Contact Lens Electrode Array for Multi-electrode Electroretinography (meERG)," IEEE, 2011, 2 pages.

Singh, et al., "Novel Approaches in Formulation and Drug Delivery using Contact Lenses," Journal of Basic and Clinical Pharmacy, May 2011, pp. 87-101, vol. 2, Issue 2.

Thomas, et al., "Functional Contact Lenses for Remote Health Monitoring in Developing Countries," IEEE Global Humanitarian Technology Conference, 2011, pp. 212-217, IEEE Computer Society.

Tweedie, et al., "Contact creep compliance of viscoelastic materials via nanoindentation," J. Mater. Res., Jun. 2006, pp. 1576-1589, vol. 21, No. 2, Materials Research Society.

Wall, K., "Active contact lens that lets you see like the Terminator patented," Feb. 10, 2012, http://vvww.patexia.com/feed/active-contact-lens-that-lets-you-see-like-the-terminator-patented-2407, Last accessed Mar. 28, 2012, 5 pages.

Zarbin, et al., "Nanotechnology in ophthalmology," Can J Ophthalmol, 2010, pp. 457-476, vol. 45, No. 5.

International Searching Authority, International Search Report and Written Opinion for PCT/US2014/016051 mailed May 13, 2014, 10 pages.

Office Action in U.S. Appl. No. 13/851,290, mailed Feb. 24, 2014.

Choi, et al., "Polymers for Flexible Displays: From Material Selection to Device Applications", Progress in Polymer Science 33 (2008), pp. 581-630.

Li, et al., "Parylene-Based Integrated Wireless Single-Channel Neurostimulator", Sensors and Actuators A: Physical, 166 (2011), pp. 193-200.

Meyer, Jorg-Uwe, "Retina Implant—A bioMEMS Challenge", Sensors and Actuators A, 97-98 (2002), pp. 1-9.

Rodger, et al., "Scalable High Lead-Count Parylene Package for Retinal Prostheses", Sensors and Actuators B, 117 (2006), pp. 107-114.

Rodger, et al., "Microelectronic Packaging for Retinal Prostheses" IEEE Engineering in Medicine and Biology Magazine, Sep./Oct. 2005, pp. 52-57.

Wang, et al., "A Bio-Inspired Two-Layer Multiple-Walled Carbon Nanotube-Polymer Composite Sensor Array and a Bio-Inspired Fast-Adaptive Readout Circuit for a Portable Electronic Nose", Biosensors and Bioelectronics 26 (2011), pp. 4301-4307.

\* cited by examiner

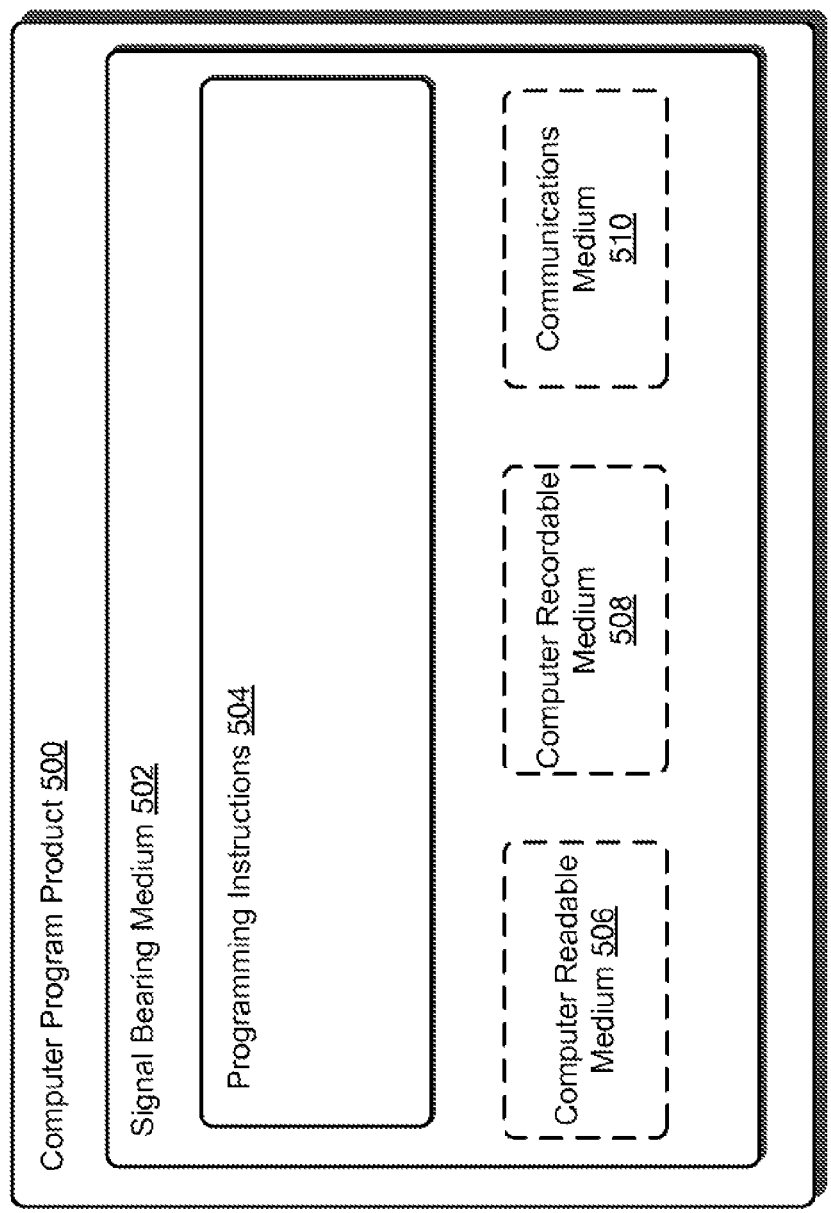

SYSTEMS AND METHODS FOR ENCAPSULATING ELECTRONICS IN A MOUNTABLE DEVICE

CROSS REFERENCE TO RELATED APPLICATIONS

The present application is a continuation of U.S. patent application Ser. No. 13/851,290, filed Mar. 27, 2013, which is currently pending. The entire disclosure contents of this application are herewith incorporated by reference into the present application.

BACKGROUND

Unless otherwise indicated herein, the materials described in this section are not prior art to the claims in this application and are not admitted to be prior art by inclusion in this section.

A mountable device may be configured to monitor health-related information based on at least one analyte detected from a user wearing the mountable device. In the instance where the mountable device is an eye-mountable device, the eye-mountable device may be in the form of a contact lens that includes a sensor apparatus configured to detect one or more analytes. The sensor apparatus may monitor health-related information of a user of the eye-mountable device, such as a glucose level. Further, the sensor apparatus may monitor various other types of health-related information.

SUMMARY

In one aspect, an example mountable device is disclosed. The mountable device includes: a polymer that defines at least one mounting surface of the mountable device; and a bio-compatible structure embedded in the polymer. The bio-compatible structure includes an electronic component that has electrical contacts on a contact surface thereof, sensor electrodes, and electrical interconnects between the sensor electrodes and the electrical contacts, and a bio-compatible material fully encapsulates the bio-compatible structure except for the sensor electrodes. The sensor electrodes are disposed on a surface of the bio-compatible material that is substantially flush with the contact surface of the electronic component.

In another aspect, an example method for fabricating a mountable device is disclosed. The method involves fabricating a bio-compatible structure that includes an electronic component and a conductive pattern, in which the electronic component has a first surface and a second surface opposite the first surface and includes electrical contacts on the second surface. Fabricating the bio-compatible structure involves: forming a first layer of a bio-compatible material; positioning the first surface of the electronic component on the first layer of the bio-compatible material; forming a second layer of the bio-compatible material over the first layer of the bio-compatible material and the second surface of the electronic component; exposing the electrical contacts on the second surface of the electronic component by removing a portion of the second layer of the bio-compatible material; after exposing the electrical contacts, forming the conductive pattern to define sensor electrodes on the second layer of the bio-compatible material and electrical interconnects between the sensor electrodes and the electrical contacts; forming a third layer of the bio-compatible material over the conductive pattern; exposing the sensor electrodes by removing a portion of the third layer of the bio-compatible material; and surrounding the bio-compatible structure with a polymer. The polymer defines at least one mounting surface of the mountable device.

In yet another aspect, an example method is disclosed. The method involves: forming a first layer of a bio-compatible material; positioning, on the first layer of the bio-compatible material, an electronic component that has a first surface and a second surface opposite the first surface and includes first electrical contacts and second electrical contacts on the second surface, such that the first surface is in contact with the first layer of the bio-compatible material; forming a second layer of the bio-compatible material over the first layer of the bio-compatible material and the second surface of the electronic component; removing a portion of the second layer of the bio-compatible material so as to expose the first electrical contacts and the second electrical contacts on the second surface of the electronic component; forming a conductive pattern that defines sensor electrodes and an antenna on the second layer of the bio-compatible material, first electrical interconnects between the sensor electrodes and the first electrical contacts, and second electrical interconnects between the antenna and the second electrical contacts; forming a third layer of the bio-compatible material over the conductive pattern; removing a portion of the third layer of the bio-compatible material so as to expose the sensor electrodes; and annealing the first, second, and third layers of the bio-compatible material to provide a bio-compatible structure that includes the electronic component and the conductive pattern. The bio-compatible material fully encapsulates the bio-compatible structure except for the sensor electrodes.

These as well as other aspects, advantages, and alternatives, will become apparent to those of ordinary skill in the art by reading the following detailed description, with reference where appropriate to the accompanying drawings.

BRIEF DESCRIPTION OF THE DRAWINGS

FIG. 5 depicts a computer-readable medium configured according to an example embodiment.

DETAILED DESCRIPTION

Figure 1:
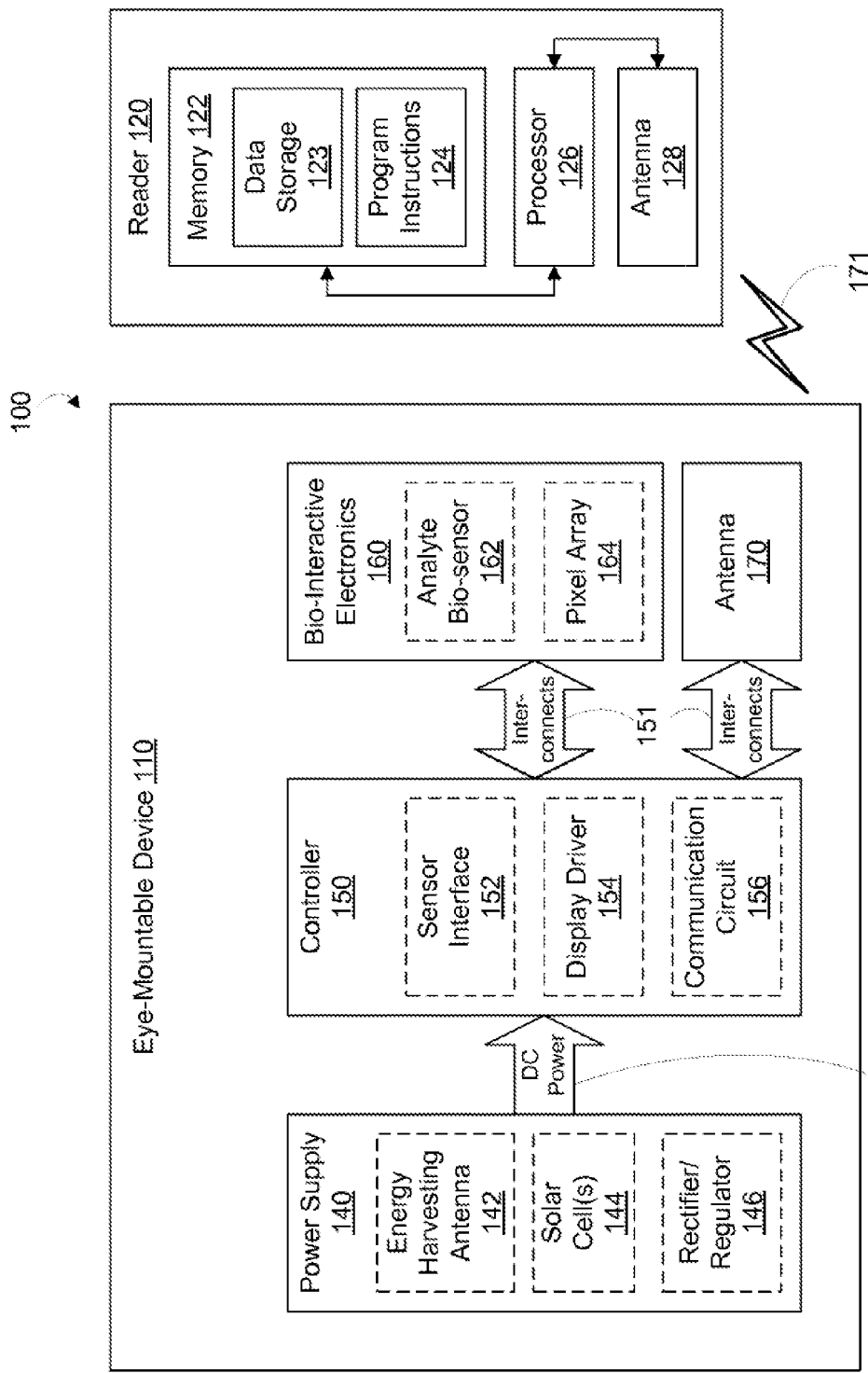
FIG. 1 is a block diagram of an example system that includes an eye-mountable device in wireless communication with an external reader.

The following detailed description describes various features and functions of the disclosed systems and methods with reference to the accompanying figures. In the figures, similar symbols typically identify similar components, unless context dictates otherwise. The illustrative embodiments described herein are not meant to be limiting. It will be readily understood that certain aspects of the present disclosure may be arranged and combined in a wide variety of different configurations, all of which are contemplated herein.

I. Overview

A mountable device may be configured to monitor health-related information based on at least one analyte detected from a user wearing the mountable device. The mountable device may include a sensing platform configured to detect the at least one analyte. The sensing platform may include a sensor apparatus, control electronics, and an antenna, and may be at least partially embedded in a polymeric material that defines at least one mounting surface of the mountable device. The control electronics operate the sensor apparatus to perform readings indicative of concentrations of an analyte and operate the antenna to wirelessly communicate the readings to an external reader.

In some examples, the mountable device could be an eye-mountable device. The eye-mountable device may be in the form of a round lens configured to mount to a corneal surface of an eye. The sensing platform may be embedded near the periphery of the eye-mountable device to avoid interference with incident light received closer to the central region of the cornea. As used throughout this disclosure, the anterior side of the eye-mountable device refers to the outward-facing side of the eye-mountable device that does not teach the eye of the wearer, whereas the posterior side of the eye-mountable device refers to the inward-facing side of the eye-mountable device that touches the eye of the wearer.

The sensor apparatus may be an electrochemical amperometric sensor, which measures a concentration of an analyte by measuring a current generated through electrochemical oxidation or reduction reactions of the analyte. The analyte diffuses to a working electrode of the sensor and is adsorbed on the working electrode. An electrochemical reaction then occurs. A reduction reaction occurs when electrons are transferred from the working electrode to the analyte, whereas an oxidation reaction occurs when electrons are transferred from the analyte to the working electrode. The direction of electron transfer is dependent upon the electrical potentials applied to the working electrode. The response (i.e., analytical signal) of the sensor is the generated current that flows between the working electrode and a counter electrode and/or reference electrode, which is used to complete a circuit with the working electrode. When the working electrode is appropriately biased, the generated current can be proportional to the reaction rate, so as to provide a measure of the concentration of the analyte surrounding the working electrode.

In some examples, the sensing platform is in the form of a bio-compatible structure. The bio-compatible structure may be encapsulated in a bio-compatible material, except for the sensor electrodes of the electrochemical sensor. The bio-compatible material can protect the electronics in the sensing platform from fluids or other materials in the surrounding environment without triggering an immune response, and the analyte can reach the exposed sensor electrodes.

The bio-compatible structure may be fabricating by positioning an electronic component on a first layer of bio-compatible material, and forming one or more layers of bio-compatible material over the electronic component and over a conductive pattern that defines the sensor electrodes, antenna, and respective electrical interconnects to respective electrical contacts on the electrical component. Then, a portion of the bio-compatible material over the sensor electrodes may be removed, for example, by etching.

II. Example Sensing Platform

FIG. 1 is a block diagram of a system 100 that includes an eye-mountable device 110 in wireless communication with an external reader 120. The eye-mountable device 110 may be a polymeric material that may be appropriately shaped for mounting to a corneal surface and in which a sensing platform is at least partially embedded. The sensing platform may include a power supply 140, a controller 150, bio-interactive electronics 160, and an antenna 170.

In some example embodiments, the sensing platform may be positioned away from the center of the eye-mountable device 110 and thereby avoid interference with light transmission to the central, light-sensitive region of the eye. For example, where the eye-mountable device 110 is shaped as a curved disk, the sensing platform may be embedded around the periphery (e.g., near the outer circumference) of the disk. In other example embodiments, the sensing platform may be positioned in or near the central region of the eye-mountable device 110. For example, portions of the sensing platform may be substantially transparent to incoming visible light to mitigate interference with light transmission to the eye. Moreover, in some embodiments, the bio-interactive electronics 160 may include a pixel array 164 that emits and/or transmits light to be received by the eye according to display instructions. Thus, the bio-interactive electronics 160 may optionally be positioned in the center of the eye-mountable device so as to generate visual cues perceivable to a wearer of the eye-mountable device 110, such as displaying information (e.g., characters, symbols, flashing patterns, etc.) on the pixel array 164.

The power supply 140 is configured to harvest ambient energy to power the controller 150 and bio-interactive electronics 160, and may include an energy harvesting antenna 142 and/or solar cells 144. The energy-harvesting antenna 142 may capture energy from incident radio radiation. The solar cells 144 may comprise photovoltaic cells configured to capture energy from incoming ultraviolet, visible, and/or infrared radiation.

A rectifier/regulator 146 may be used to condition the captured energy to a stable DC supply voltage 141 at a level suitable for operating the controller, and then supply the voltage to the controller 150. The rectifier/regulator 146 may include one or more energy storage devices to mitigate high frequency variations in the ambient energy gathering antenna 142 and/or solar cell(s) 144. For example, one or more energy storage devices (e.g., a capacitor or an inductor) may be connected in parallel across the outputs of the rectifier 146 to regulate the DC supply voltage 141 and may be configured to function as a low-pass filter.

The controller 150 is configured to execute instructions to operate the bio-interactive electronics 160 and the antenna 170. The controller 150 includes logic circuitry configured to operate the bio-interactive electronics 160 so as to interact with a biological environment of the eye-mountable device 110. The interaction could involve the use of one or more components, such an analyte bio-sensor 162 in the bio-interactive electronics 160, to obtain input from the biological environment. Additionally or alternatively, the interaction could involve the use of one or more components, such as a pixel array 164, to provide an output to the biological environment.

In one example, the controller 150 includes a sensor interface module 152 that is configured to operate the analyte bio-sensor 162. The analyte bio-sensor 162 may be, for example, an amperometric electrochemical sensor that includes a working electrode and a reference electrode driven by a sensor interface. A voltage is applied between the working and reference electrodes to cause an analyte to undergo an electrochemical reaction (e.g., a reduction and/or oxidation reaction) at the working electrode. The electrochemical reaction generates an amperometric current that can be measured through the working electrode. The amperometric current can be dependent on the analyte concentration. Thus, the amount of the amperometric current that is measured through the working electrode can provide an indication of analyte concentration. In some embodiments, the sensor interface module 152 can be a potentiostat configured to apply a voltage difference between working and reference electrodes while measuring a current through the working electrode.

In some instances, a reagent may also be included to sensitize the electrochemical sensor to one or more desired analytes. For example, a layer of glucose oxidase ("GOD") proximal to the working electrode can catalyze glucose oxidation to generate hydrogen peroxide ($H_2O_2$). The hydrogen peroxide can then be electro-oxidized at the working electrode, which releases electrons to the working electrode, resulting in an amperometric current that can be measured through the working electrode.

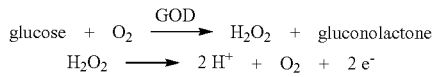

$$\text{glucose} + O_2 \xrightarrow{\text{GOD}} H_2O_2 + \text{gluconolactone}$$
$$H_2O_2 \longrightarrow 2H^+ + O_2 + 2e^-$$

The current generated by either reduction or oxidation reactions is approximately proportionate to the reaction rate. Further, the reaction rate is dependent on the rate of analyte molecules reaching the electrochemical sensor electrodes to fuel the reduction or oxidation reactions, either directly or catalytically through a reagent. In a steady state, where analyte molecules diffuse to the electrochemical sensor electrodes from a sampled region at approximately the same rate that additional analyte molecules diffuse to the sampled region from surrounding regions, the reaction rate is approximately proportionate to the concentration of the analyte molecules. The current measured through the working electrode thus provides an indication of the analyte concentration.

The controller 150 may also include a display driver module 154 for operating a pixel array 164. The pixel array 164 is an array of separately programmable light transmitting, light reflecting, and/or light emitting pixels arranged in rows and columns. The individual pixel circuits can optionally include liquid crystal technologies, microelectromechanical technologies, emissive diode technologies, etc. to selectively transmit, reflect, and/or emit light according to information from the display driver module 154. Such a pixel array 164 may also include more than one color of pixels (e.g., red, green, and blue pixels) to render visual content in color. The display driver module 154 can include, for example, one or more data lines providing programming information to the separately programmed pixels in the pixel array 164 and one or more addressing lines for setting groups of pixels to receive such programming information. Such a pixel array 164 situated on the eye can also include one or more lenses to direct light from the pixel array to a focal plane perceivable by the eye.

The controller 150 may also include a communication circuit 156 for sending and/or receiving information via the antenna 170. The communication circuit 156 may include one or more oscillators, mixers, frequency injectors, or the like to modulate and/or demodulate information on a carrier frequency to be transmitted and/or received by the antenna 170. In some example embodiments, the eye-mountable device 110 is configured to indicate an output from a bio-sensor by modulating an impedance of the antenna 170 in a manner that is perceivable by the external reader 120. For example, the communication circuit 156 can cause variations in the amplitude, phase, and/or frequency of backscatter radiation from the antenna 170, and such variations may then be detected by the reader 120.

The controller 150 is connected to the bio-interactive electronics 160 and the antenna 170 via interconnects 151. The interconnects 151 may comprise a patterned conductive material (e.g., gold, platinum, palladium, titanium, copper, aluminum, silver, metals, any combinations of these, etc.).

It is noted that the block diagram shown in FIG. 1 is described in connection with functional modules for convenience in description. However, embodiments of the eye-mountable device 110 can be arranged with one or more of the functional modules ("sub-systems") implemented in a single chip, integrated circuit, and/or physical component.

Additionally or alternatively, the energy harvesting antenna 142 and the communication antenna 170 can be implemented in the same, dual-purpose antenna. For example, a loop antenna can both harvest incident radiation for power generation and communicate information via backscatter radiation.

The external reader 120 includes an antenna 128 (or group of more than one antennae) to send and receive wireless signals 171 to and from the eye-mountable device 110. The external reader 120 also includes a computing system with a processor 126 in communication with a memory 122. The memory 122 is a non-transitory computer-readable medium that can include, without limitation, magnetic disks, optical disks, organic memory, and/or any other volatile (e.g. RAM) or non-volatile (e.g. ROM) storage system readable by the processor 126. The memory 122 includes a data storage 123 to store indications of data, such as sensor readings (e.g., from the analyte bio-sensor 162), program settings (e.g., to adjust behavior of the eye-mountable device 110 and/or external reader 120), etc. The memory 122 also includes program instructions 124 for execution by the processor 126. For example, the program instructions 124 may cause the external reader 120 to provide a user interface that allows for retrieving information communicated from the eye-mountable device 110 (e.g., sensor outputs from the analyte bio-sensor 162). The external reader 120 may also include one or more hardware components for operating the antenna 128 to send and receive the wireless signals 171 to and from the eye-mountable device 110. For example, oscillators, frequency injectors, encoders, decoders, amplifiers, and filters can drive the antenna 128 according to instructions from the processor 126.

The external reader 120 may be a smart phone, digital assistant, or other portable computing device with wireless connectivity sufficient to provide the wireless communication link 171. The external reader 120 may also be implemented as an antenna module that can be plugged in to a portable computing device, such as in an example where the communication link 171 operates at carrier frequencies not commonly employed in portable computing devices. In some instances, the external reader 120 is a special-purpose device configured to be worn relatively near a wearer's eye to allow the wireless communication link 171 to operate using little or low power. For example, the external reader 120 can be integrated in a piece of jewelry such as a necklace, earing, etc. or integrated in an article of clothing worn near the head, such as a hat, headband, etc.

In an example where the eye-mountable device 110 includes an analyte bio-sensor 162, the system 100 can be operated to monitor the analyte concentration in tear film on the surface of the eye. To perform a reading with the system 100 configured as a tear film analyte monitor, the external reader 120 can emit radio frequency radiation 171 that is harvested to power the eye-mountable device 110 via the power supply 140. Radio frequency electrical signals captured by the energy harvesting antenna 142 (and/or the communication antenna 170) are rectified and/or regulated in the rectifier/regulator 146 and a regulated DC supply voltage 147 is provided to the controller 150. The radio frequency radiation 171 thus turns on the electronic components within the eye-mountable device 110. Once turned on, the controller 150 operates the analyte bio-sensor 162 to measure an analyte concentration level. For example, the sensor interface module 152 can apply a voltage between a working electrode and a reference electrode in the analyte bio-sensor 162. The applied voltage can be sufficient to cause the analyte to undergo an electrochemical reaction at the working electrode and thereby generate an amperometric current that can be measured through the working electrode. The measured amperometric current can provide the sensor reading ("result") indicative of the analyte concentration. The controller 150 can operate the antenna 170 to communicate the sensor reading back to the external reader 120 (e.g., via the communication circuit 156).

In some embodiments, the system 100 can operate to non-continuously ("intermittently") supply energy to the eye-mountable device 110 to power the controller 150 and electronics 160. For example, radio frequency radiation 171 can be supplied to power the eye-mountable device 110 long enough to carry out a tear film analyte concentration measurement and communicate the results. For example, the supplied radio frequency radiation can provide sufficient power to apply a potential between a working electrode and a reference electrode sufficient to induce electrochemical reactions at the working electrode, measure the resulting amperometric current, and modulate the antenna impedance to adjust the backscatter radiation in a manner indicative of the measured amperometric current. In such an example, the supplied radio frequency radiation 171 can be considered an interrogation signal from the external reader 120 to the eye-mountable device 110 to request a measurement. By periodically interrogating the eye-mountable device 110 (e.g., by supplying radio frequency radiation 171 to temporarily turn the device on) and storing the sensor results (e.g., via the data storage 123), the external reader 120 can accumulate a set of analyte concentration measurements over time without continuously powering the eye-mountable device 110.

Figure 2A:
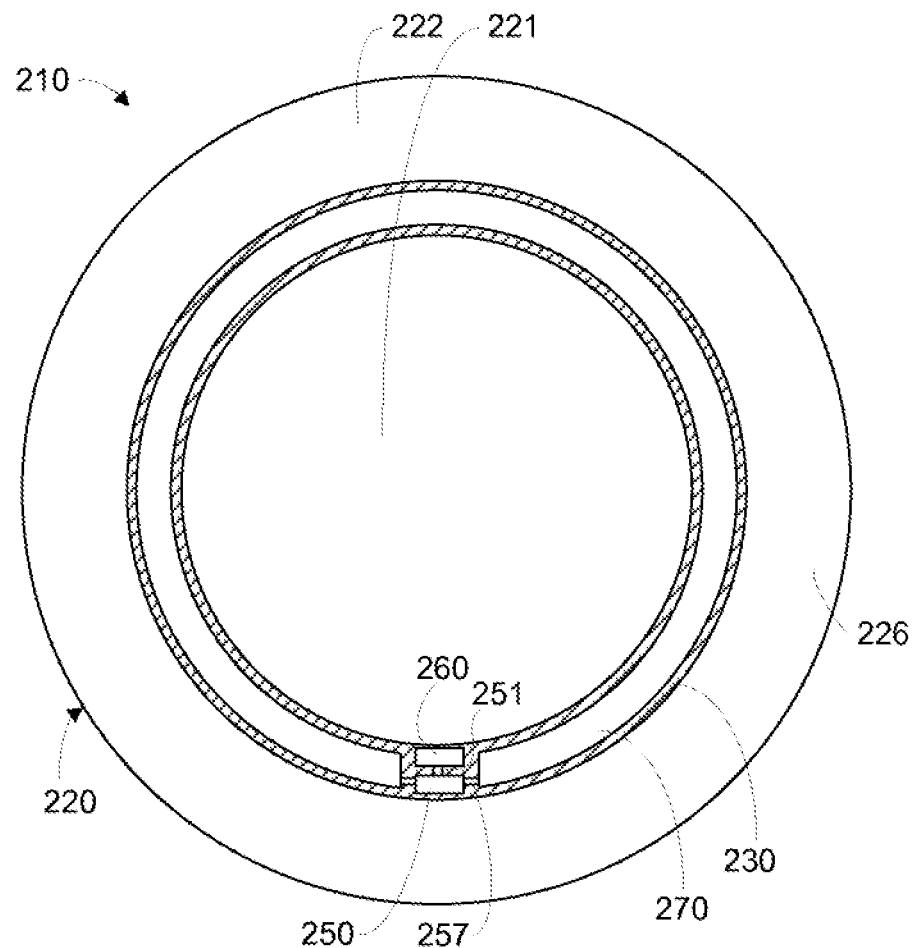
FIG. 2A is a bottom view of an example eye-mountable device.
Figure 2B:
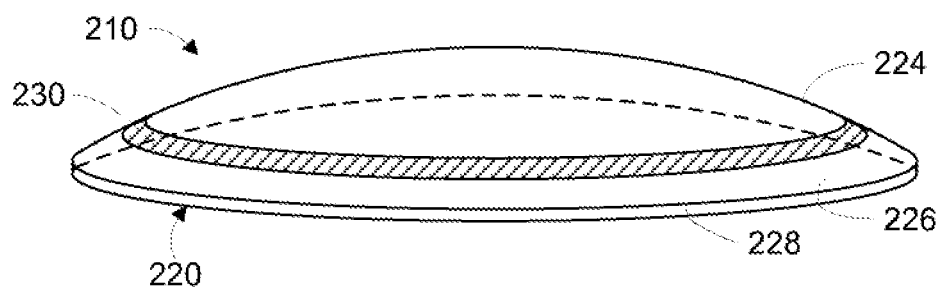
FIG. 2B is a side view of the example eye-mountable device of FIG. 2A.

FIG. 2A is a bottom view of an example eye-mountable device 210. FIG. 2B is an aspect view of the example eye-mountable device 210. It is noted that relative dimensions in FIGS. 2A and 2B are not necessarily to scale, but have been rendered for purposes of explanation only in describing the arrangement of the example eye-mountable device 210.

The eye-mountable device 210 may include a polymeric material 220, which may be a substantially transparent material to allow incident light to be transmitted to the eye. The polymeric material 220 may include one or more bio-compatible materials similar to those employed to form vision correction and/or cosmetic contact lenses in optometry, such as polyethylene terephthalate ("PET"), polymethyl methacrylate ("PMMA"), polyhydroxyethylmethacrylate ("polyHEMA"), silicone hydrogels, or any combinations of these. Other polymeric materials may also be envisioned. The polymeric material 220 may include materials configured to moisturize the corneal surface, such as hydrogels and the like. In some embodiments, the polymeric material 220 is a deformable ("non-rigid") material to enhance wearer comfort.

To facilitate contact-mounting, the eye-mountable device 210 may comprise a concave surface 226 configured to adhere ("mount") to a moistened corneal surface (e.g., by capillary forces with a tear film coating the corneal surface). The bottom view in FIG. 2A faces the concave surface 226. While mounted with the concave surface against the eye, a convex surface 224 of eye-mountable device 210 is formed so as not to interfere with eye-lid motion while the eye-mountable device 210 is mounted to the eye. From the bottom view shown in FIG. 2A, an outer periphery 222, near the outer circumference of the eye-mountable device 210 has a concave curve shape, whereas a central region 221, near the center of the eye-mountable device 210, has a convex curve shape.

The eye-mountable device 210 can have dimensions similar to a vision correction and/or cosmetic contact lenses, such as a diameter of approximately 1 centimeter, and a thickness of about 0.1 to about 0.5 millimeters. However, the diameter and thickness values are provided for explanatory purposes only. In some embodiments, the dimensions of the eye-mountable device 210 may be selected according to the size and/or shape of the corneal surface of the wearer's eye. In some embodiments, the eye-mountable device 210 is shaped to provide a predetermined, vision-correcting optical power, such as provided by a prescription contact lens.

A sensing platform 230 is embedded in the eye-mountable device 210. The sensing platform 230 can be embedded to be situated near or along the outer periphery 222, away from the central region 221. Such a position ensures that the sensing platform 230 will not interfere with a wearer's vision when the eye-mountable device 210 is mounted on a wearer's eye, because it is positioned away from the central region 221 where incident light is transmitted to the eye-sensing portions of the eye. Moreover, portions of the sensing platform 230 can be formed of a transparent material to further mitigate effects on visual perception.

The sensing platform 230 may be shaped as a flat, circular ring (e.g., a disk with a centered hole). The flat surface of the sensing platform 230 (e.g., along the radial width) allows for mounting electronics such as chips (e.g., via flip-chip mounting) and for patterning conductive materials to form electrodes, antenna(e), and/or interconnections. The sensing platform 230 and the polymeric material 220 may be approximately cylindrically symmetric about a common central axis. The sensing platform 230 may have, for example, a diameter of about 10 millimeters, a radial width of about 1 millimeter (e.g., an outer radius 1 millimeter greater than an inner radius), and a thickness of about 50 micrometers. These dimensions are provided for example purposes only, and in no way limit the present disclosure.

A loop antenna 270, controller 250, and bio-interactive electronics 260 are included in the sensing platform 230. The controller 250 may be a chip including logic elements configured to operate the bio-interactive electronics 260 and the loop antenna 270, and may be the same as or similar to the controller 150 discussed in connection with FIG. 1. The controller 250 is electrically connected to the loop antenna 270 by interconnects 257 also situated on the substrate 230. Similarly, the controller 250 is electrically connected to the bio-interactive electronics 260 by an interconnect 251. The interconnects 251, 257, the loop antenna 270, and any conductive electrodes (e.g., for an electrochemical analyte bio-sensor, etc.) may be formed from any type of conductive material and may be patterned by any process that be used for patterning such materials, such as deposition or photolithography, for example. The conductive materials patterned on the substrate 230 may be, for example, gold, platinum, palladium, titanium, carbon, aluminum, copper, silver, silver-chloride, conductors formed from noble materials, metals, or any combinations of these materials. Other materials may also be envisioned.

Figure 2D:
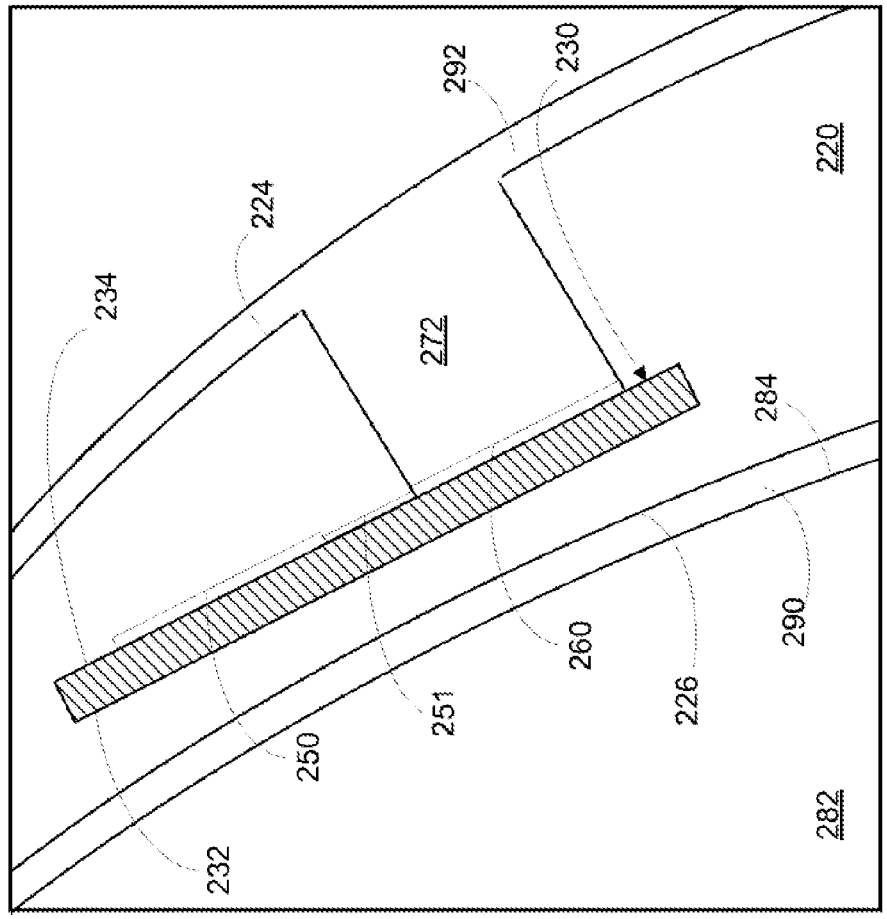
FIG. 2D is an enlarged partial view of the cross-section of the example eye-mountable device shown in FIG. 2C.

As shown in FIG. 2A, the bio-interactive electronics module 260 is on a side of the sensing platform 230 facing the convex surface 224. Where the bio-interactive electronics module 260 includes an analyte bio-sensor, for example, mounting such a bio-sensor on the sensing platform 230 to be close to the convex surface 224 allows the bio-sensor to sense analyte that has diffused through convex surface 224 or has reached the bio-sensor through a channel in the convex surface 224 (FIGS. 2C and 2D show a channel 272).

The loop antenna 270 is a layer of conductive material patterned along the flat surface of the substrate 230 to form a flat conductive ring. The loop antenna 270 may be the same as or similar to the antenna 170 described in connection with FIG. 1. In some example embodiments, the loop antenna 270 does not form a complete loop. For example, the loop antenna 270 may include a cutout to allow room for the controller 250 and bio-interactive electronics 260, as illustrated in FIG. 2A. However, in another example embodiment, the loop antenna 270 can be arranged as a continuous strip of conductive material that wraps entirely around the sensing platform 230 one or more times. Interconnects between the ends of such a wound antenna (e.g., the antenna leads) can connect to the controller 250 in the sensing platform 230.

The sensing platform 230 may be a bio-compatible structure in which some or all of the components are encapsulated by a bio-compatible material. In one example, controller 250, interconnects 251, 257, bio-interactive electronics 260, and antenna 270 are fully encapsulated by bio-compatible material, except for the sensor electrodes in the bio-interactive electronics 260.

Figure 2C:
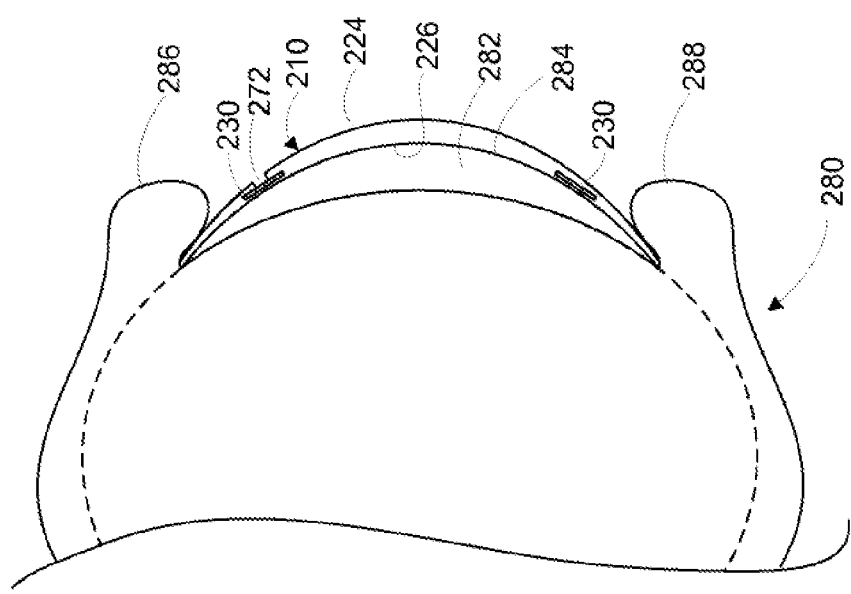
FIG. 2C is a side cross-section view of the example eye-mountable device of FIG. 2A mounted to a corneal surface of an eye.

FIG. 2C is a side cross-section view of the example eye-mountable electronic device 210 mounted to a corneal surface 284 of an eye 280. FIG. 2D is an enlarged partial view the cross-section of the example eye-mountable device shown in FIG. 2C. It is noted that relative dimensions in FIGS. 2C and 2D are not necessarily to scale, but have been rendered for purposes of explanation only in describing the arrangement of the example eye-mountable electronic device 210. Some aspects are exaggerated to allow for illustration and to facilitate explanation.

The eye 280 includes a cornea 282 that is covered by bringing an upper eyelid 286 and a lower eyelid 288 together over the surface of the eye 280. Incident light is received by the eye 280 through the cornea 282, where light is optically directed to light sensing elements of the eye 280 to stimulate visual perception. The motion of the upper and lower eyelids 286, 288 distributes a tear film across the exposed corneal surface 284 of the eye 280. The tear film is an aqueous solution secreted by the lacrimal gland to protect and lubricate the eye 280. When the eye-mountable device 210 is mounted in the eye 280, the tear film coats both the concave and convex surfaces 224, 226, providing an inner layer 290 (along the concave surface 226) and an outer layer 292 (along the convex surface 224). The inner layer 290 on the corneal surface 284 also facilitates mounting the eye-mountable device 210 by capillary forces between the concave surface 226 and the corneal surface 284. In some embodiments, the eye-mountable device 210 can also be held over the eye 280 in part by vacuum forces against the corneal surface 284 due to the curvature of the concave surface 226. The tear film layers 290, 292 may be about 10 micrometers in thickness and together account for about 10 microliters of fluid.

The tear film is in contact with the blood supply through capillaries in the structure of the eye and includes many biomarkers found in blood that are analyzed to diagnose health states of an individual. For example, tear film includes glucose, calcium, sodium, cholesterol, potassium, other biomarkers, etc. The biomarker concentrations in tear film can be systematically different than the corresponding concentrations of the biomarkers in the blood, but a relationship between the two concentration levels can be established to map tear film biomarker concentration values to blood concentration levels. For example, the tear film concentration of glucose can be established (e.g., empirically determined) to be approximately one tenth the corresponding blood glucose concentration. Although another ratio relationship and/or a non-ratio relationship may be used. Thus, measuring tear film analyte concentration levels provides a non-invasive technique for monitoring biomarker levels in comparison to blood sampling techniques performed by lancing a volume of blood to be analyzed outside a person's body.

As shown in the cross-sectional views in FIGS. 2C and 2D, the sensing platform 230 can be inclined so as to be approximately parallel to the adjacent portion of the convex surface 224. As described above, the sensing platform 230 is a flattened ring with an inward-facing surface 232 (closer to the concave surface 226 of the polymeric material 220) and an outward-facing surface 234 (closer to the convex surface 224). The sensing platform 230 can include electronic components and/or patterned conductive materials adjacent to either or both surfaces 232, 234.

As shown in FIG. 2D, the bio-interactive electronics 260, the controller 250, and the conductive interconnect 251 are mounted on the outward-facing surface 234 such that the bio-interactive electronics 260 are facing the convex surface 224. With this arrangement, the bio-interactive electronics 260 can receive analyte concentrations in the tear film 292 through the channel 272. However, in other examples, the bio-interactive electronics 260 may be mounted on the inward-facing surface 232 of the sensing platform 230 such that the bio-interactive electronics 260 are facing the concave surface 226.

III. Fabrication of an Example Bio-Compatible Structure

FIGS. 3A-3K illustrate stages in a process for fabricating a bio-compatible structure, such as sensing platform 230. The illustrations shown in FIG. 3A-3K are generally shown in cross-sectional views to illustrate sequentially formed layers developed to create the bio-compatible structure that encapsulates electronics. The layers can be developed by microfabrication and/or manufacturing techniques such as, for example, electroplating, photolithography, deposition, and/or evaporation fabrication processes and the like. The various materials may be formed according to patterns using photoresists and/or masks to pattern materials in particular arrangements, such as to form wires, electrodes, connection pads, etc. Additionally, electroplating techniques may also be employed to coat an arrangement of electrodes with a metallic plating. For example, an arrangement of conductive material formed by a deposition and/or photolithography process can be plated with a metallic material to create a conductive structure with a desired thickness. However, the dimensions, including relative thicknesses, of the various layers illustrated and described in connection with FIGS. 3A-3K to create an encapsulated electronics structure are not illustrated to scale. Instead, the drawings in FIGS. 3A-3K schematically illustrate the ordering of the various layers for purposes of explanation only.

Figure 3A:
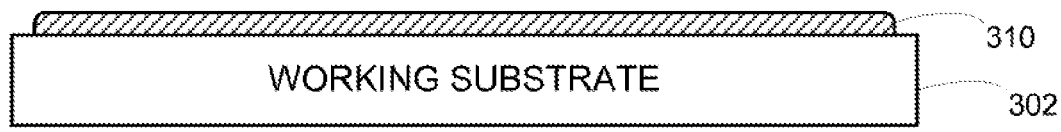
FIGS. 3A-3K show stages of fabricating an example bio-compatible structure in which an electronics module is encapsulated in a bio-compatible material.

FIG. 3A illustrates a working substrate 302 coated with a first layer of bio-compatible material 310. The working substrate 302 may be any flat surface on which the layers of the encapsulated electronics structure can be assembled. For example, the working substrate 302 may be a wafer (e.g., a silicon wafer) similar to those used in the fabrication of semiconductor device and/or microelectronics.

The first layer of bio-compatible material 310 may include a polymeric material such as parylene C (e.g., dichlorodi-p-xylylene), a polyethylene terephthalate (PET), a polydimethylsiloxane (PDMS), other silicone elastomers, and/or another bio-compatible polymeric material. Bio-compatibility refers generally to the ability of a material or device to co-exist with a biological host. Bio-compatible materials are generally those that do not bring about a host response (such as an immune response) that results in deleterious effects to either the biological host or the material. In addition to being bio-compatible, the first layer of bio-compatible material 310 may be an electrically insulating material to isolate the encapsulated electronics from the surrounding environment (e.g., from current-carrying particles and/or fluids).

The first layer of bio-compatible material 310 may be formed by a microfabrication process such as vapor deposition on top of the working substrate 302, and provides a surface on which the encapsulated electronics structure can be formed. The first layer of bio-compatible material 310 may be deposited onto the working substrate 302 with a substantially uniform thickness such that the surface of the bio-compatible material 310 opposite the working substrate 302 forms a flat surface. The first layer of bio-compatible material 310 may comprise a thickness in the range of 1-50 micrometers, in one example embodiment.

Figure 3B:
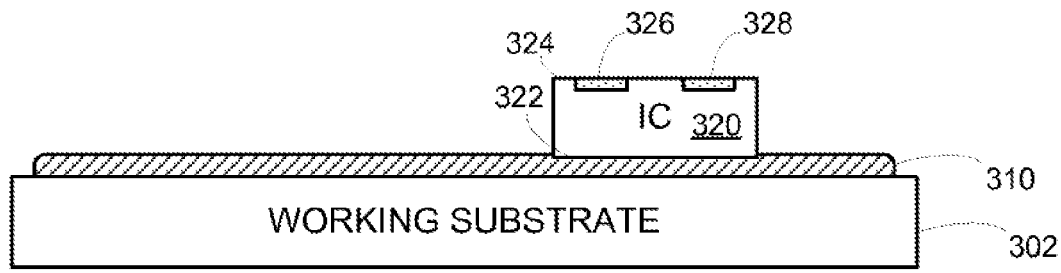

FIG. 3B illustrates a chip 320 mounted to the first layer of bio-compatible material 310. The chip 320 could include, for example, one or more integrated circuits (ICs) and/or one or more discrete electronic components, such as a controller similar to the controller 150 of FIG. 1. Heat, pressure, a pick-and-place tool, or a flip-chip bonder, for example, may be used to adhere a first surface 322 of the chip 320 to the first layer of bio-compatible material 310. Chip 320 has a second surface 324 opposite the first surface 322 that includes first electrical contacts 326 and second electrical contacts 328.

Figure 3C:
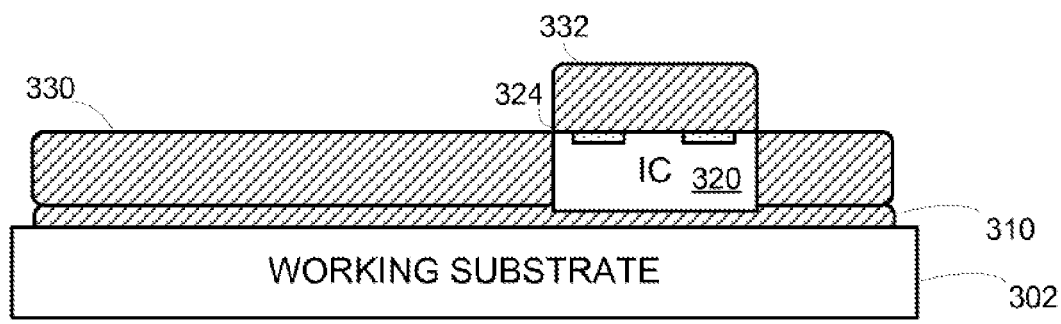

As shown in FIG. 3C, a second layer of bio-compatible material 330 is then formed over the first layer of bio-compatible material 310 and the chip 320. The second layer of bio-compatible material 330 is applied until the thickness of each of the portions of the layer formed directly on top of the first layer 310 is substantially flush with the second surface 324 of the chip 320. The second layer of bio-compatible material 330 may be evenly applied over both the exposed first layer as well as the chip 320 that is placed on top of the first layer, such that a portion of the second layer 330 will form on top of the second surface 324 of the chip 320. Such a portion of the second layer 330 formed on top of the chip 320 is shown in FIG. 3C as portion 332.

Figure 3D:
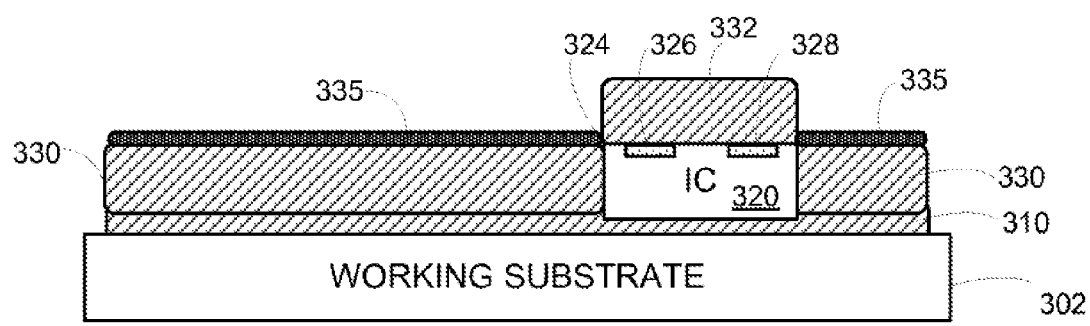

As shown in FIG. 3D, a masking layer 335 may next be formed over the entire second layer 330 except for the portion 332 of the second layer 330 that is formed on top of the second surface 324 of the chip 320. In some examples, the masking layer 335 is a metal mask and may be made using photolithography or metal deposition (evaporation or sputtering).

Figure 3E:
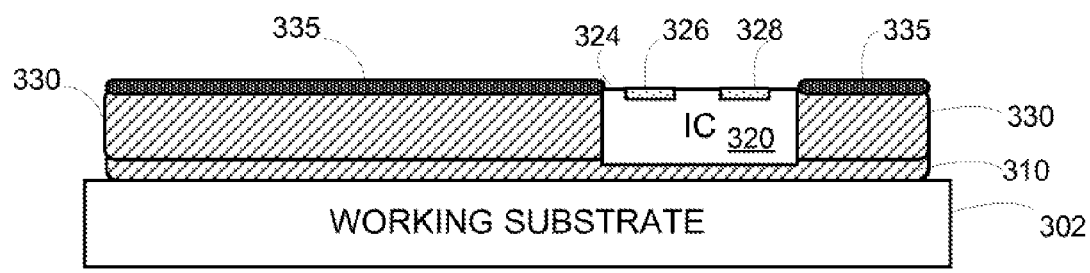

The silicon wafer and materials on the wafer are then exposed to a plasma. The plasma may comprise a plasma asher, a reactive ion etcher, inductively coupled plasma, etc. The plasma will etch through any exposed layers of bio-compatible material, through such layers down to the working substrate 302; however, the plasma will not etch the masking layer or the chip 320. The masking layer thus serves to block the applied plasma from etching anything directly underneath the masking layer. Various other components, such as the chip 320, may also serve as a mask to block the plasma from etching layers of bio-compatible material that are directly under the components. Thus, as shown in FIG. 3E, the plasma has etched away the portion 332 of the second layer of bio-compatible material 330 down to the chip 320. The remaining portions of the second layer of bio-compatible material 330 are protected from plasma etching by the masking layer.

Figure 3F:
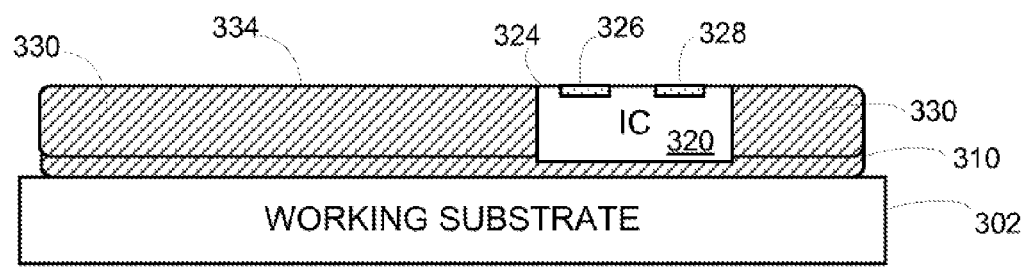

After application of plasma, the masking layer is removed, as shown in FIG. 3F. The masking layer may be removed by any number of methods. For example, if the masking layer is a metal mask, the removal may include applying a wet etch. What remains after application of the plasma and removal of the masking layer is shown in FIG. 3F: a second layer of bio-compatible material 330 having a top surface 334 that is level with the exposed, second surface 324 of the chip 320.

Figure 3G:
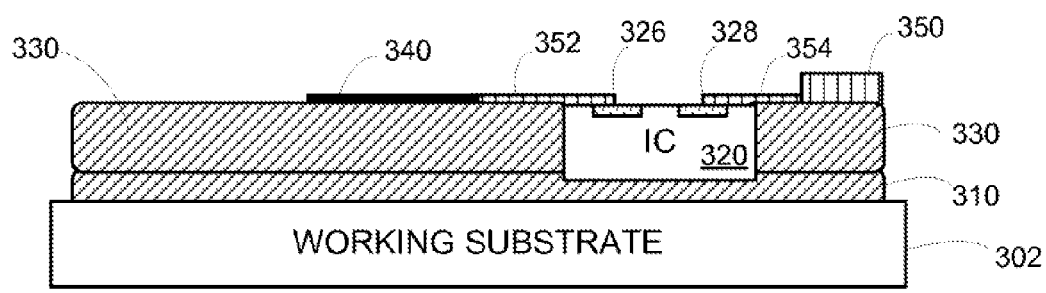

Next, a conductive pattern be fabricated directly onto the second layer of bio-compatible material 330 the first electrical contacts 326, and the second electrical contacts 328, as shown in FIG. 3G. For example, metal can be patterned onto the second layer of bio-compatible material 330 to create components for an electrochemical bio-sensor circuit powered by harvested radio frequency energy, similar to the example embodiment described above in connection with FIG. 1. In such an example embodiment, metal can be pattered to form components including sensor electrodes 340, an antenna 350, and interconnects 352, 354. The sensor electrodes 340 may include a working electrode and a reference and/or counter electrode of an electrochemical sensor, for example, as discussed in connection with FIG. 1.

The antenna 350 may be a loop antenna suitable for receiving radio frequency radiation harvested to provide a power supply to the electronics. The antenna 350 may be, for example, a loop with a radius of approximately 5 millimeters that is suitable for being arranged around the perimeter of an eye-mountable device, similar to the antenna illustrated and described in connection with FIGS. 1 and 2A-2D above. The sensor electrodes 340, the interconnects 352, 354, and the antenna 350 can each be formed with a thickness of about 5 micrometers, for example.

The interconnects 352, 354 can be wires formed by photolithography, evaporation, and/or electroplating. The interconnects 352 electrically connect the sensor electrodes 340 to the first electrical contacts 326 on chip 320. The interconnects 354 electrically connect the antenna 350 to the second electrical contacts on chip 328.

The second layer of bio-compatible material 330 may comprise sufficient structural rigidity to be used as a substrate for assembling the components. The components may be formed of conductive material such as platinum, silver, gold, palladium, titanium, copper, chromium, nickel, aluminum, other metals or conductive materials, and combinations thereof. Some example embodiments may employ a substantially transparent conductive material for at least some of the electronics circuitry (e.g., a material such as indium tin oxide).

In some example embodiments, one or more of the components patterned onto the first layer of bio-compatible material 310 may be a multi-layer arrangement that includes a seed layer (or adhesion layer) patterned directly on the second layer of bio-compatible material 330. Such a seed layer can be used to adhere to both the bio-compatible material and the bulk of the metal structure that is patterned over the seed layer. For example, such a seed layer may be a material that adheres well to the bio-compatible material, and also serves as a guide to electroplate the remainder of the metal structure that forms the component.

Figure 3H:
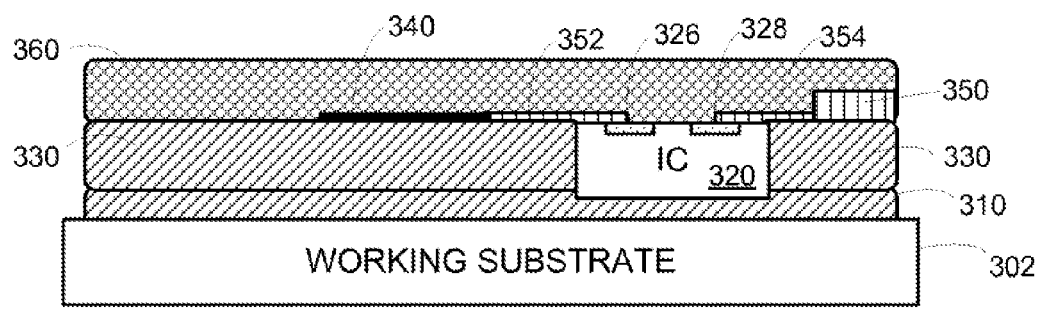

Next, a third layer of bio-compatible material 360, shown in FIG. 3H, is formed over the assembled electronic components (i.e., the chip 320, the sensor electrodes 340, the antenna 350, and the interconnects 352, 354) and the remaining exposed second layer of bio-compatible material 330. The third layer of bio-compatible material 360 functions similar to the first layer of bio-compatible material 310 to create a bio-compatible exterior surface and also electrically isolate the electronics from the surrounding environment. In addition, the third layer of bio-compatible material 360 structurally supports the assembled electronics and holds the various components in place. The third layer of bio-compatible material 350 can stabilize the chip 320 by surrounding the chip 320 to fill gaps surrounding the chip 320 (and thereby prevent movement of the chip). In some examples, the deposition of the third layer of bio-compatible material 360 results in a conformal coating over the assembled electronics. The third layer of bio-compatible material 360 can have a thickness in the range of about 1 to 50 micrometers, for example.

The third layer of bio-compatible material 360 can be formed of the same or substantially similar material to the first and the second layers of bio-compatible material 310, 330, or can optionally be a different polymeric material that is both bio-compatible and electrically insulating.

The third layer of bio-compatible material 360 is preferably deposited to create a continuous layer that spans the entirety of the assembled electronics. The third layer of bio-compatible material 360 can span a region that extends beyond a footprint of the assembled electronics. As a result, the assembled electronics can be surrounded by portions of the third layer of bio-compatible material 360 that rest directly on the second layer of bio-compatible material 330.

Figure 3I:
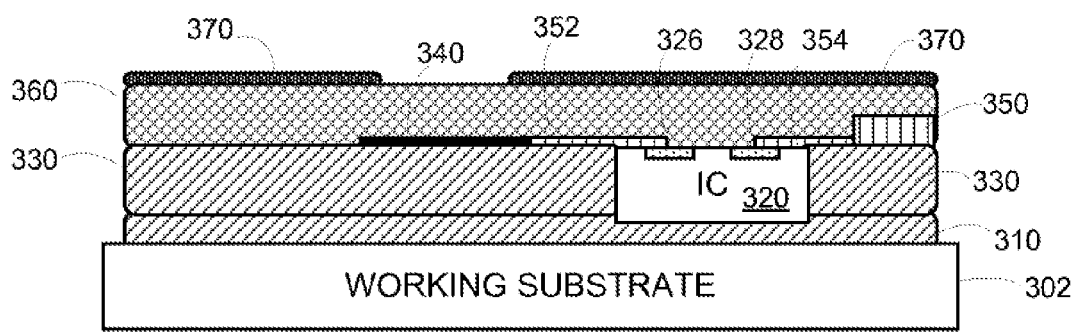

Next, as shown in FIG. 3I, a second masking layer 370 is applied on top of the third layer of bio-compatible material 360 in the shape of a flattened ring, for example, similar to the shape of the sensing platform 230 illustrated and described in connection with FIG. 2A above. The second masking layer 370 covers the assembled electronics with the exception of at least a portion of the area directly above the sensor electrodes 340. Again, in some examples, the masking layer 370 is a metal mask and may be made using photolithography or metal deposition (evaporation or sputtering).

Figure 3J:
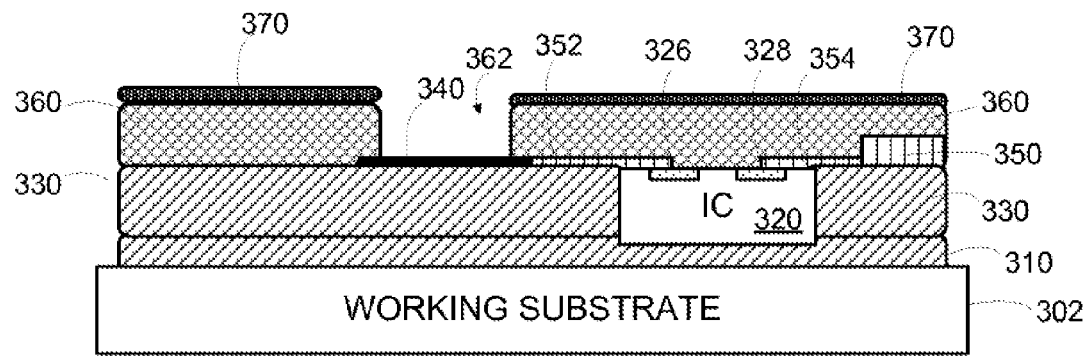

The silicon wafer and materials on the wafer are then again exposed to a plasma. The plasma may comprise plasma asher, a reactive ion etcher, inductively coupled plasma, etc. The plasma will not etch through the second masking layer or exposed electronic components, such as the sensor apparatus 340. As shown in FIG. 3J, the plasma etches the exposed third layer of bio-compatible material 360 leaving an opening 362. The plasma may also etch any exposed layers of bio-compatible material underneath the third layer, all the way down to the working substrate 302. The remaining portions of the third layer of bio-compatible material 360 are protected from plasma etching by the second masking layer 370, and the remaining portions of the first and second layers may be protected by components residing directly above those layers.

Figure 3K:
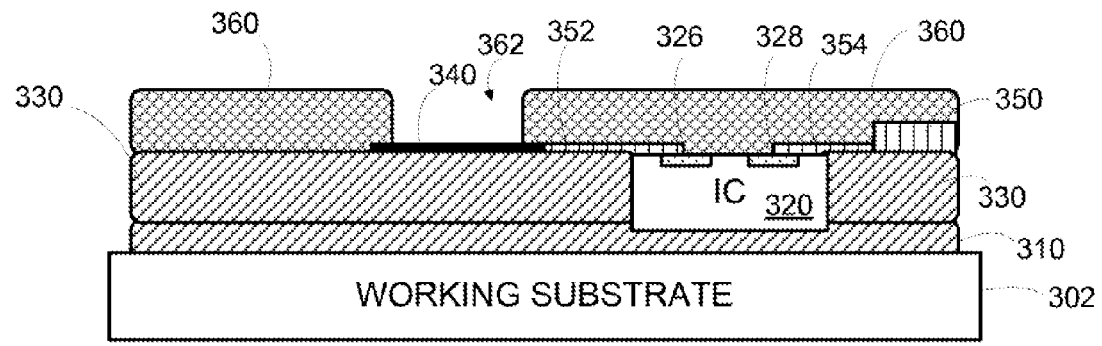

As shown in FIG. 3K, after application of plasma, the second masking layer 370 is removed. The second masking layer 370 may be removed by any number of methods. For example, if the second masking layer 370 is a metal, the removal may include applying a wet etch. What remains after application of the plasma and removal of the second masking layer 370 is shown in FIG. 3K. Thus, the third layer of bio-compatible material 360 covers the components except for an opening 362 over at least a portion of the sensor electrodes 340. Additionally, as discussed above, the second masking layer 370 was formed in a flattened ring shape and thus various layers of bio-compatible material that did not form the ring shape and did not have metal components directly above were removed by the plasma. An example top view of a possible resulting ring shape of the device is shown as the sensing platform 230 in FIG. 2A.

While not specifically shown in FIGS. 3A-3K, some fabrication processes may include forming a reagent layer proximal to the sensor electrodes 340 (e.g., covering at least the working electrode in sensor electrodes 340). The reagent layer may include a substance used to sensitize the electrodes on the sensor electrodes 340 to a particular analyte. For example a layer including glucose oxidase may be applied to the sensor electrodes 340 for detection of glucose.

To encapsulate the bio-compatible structure in the bio-compatible material, the first layer 310, the second layer 330, and the third layer 360 of the bio-compatible material can be annealed so that these layers seal together. The annealing can be performed by placing the entire assembled structure, including the working substrate 302, in an oven at a temperature sufficient to anneal the bio-compatible material in the first, second, and third layers 310, 330, 360. For example, parylene C (e.g., dichlorodi-p-xylylene) can be annealed at a temperature of approximately 150 to 200 degrees Celsius. Other bio-compatible polymeric materials (such as PET, PDMS, etc.) may require higher or lower annealing temperatures. Once cooled, the result is a bio-compatible structure in which a sealed, continuous layer of bio-compatible material encapsulates the assembled electronics within, except for the sensor electrodes 340.

Finally, the bio-compatible structure is released from the working substrate 302. In one example, the bio-compatible structure can be peeled away from the working substrate 302 following the annealing process. The encapsulated electronics structure may also be etched (e.g., application of an oxygen plasma) to remove excess bio-compatible material prior to peeling away the structure. For example, bio-compatible material may at least partially wrap around the working substrate 302 either during the deposition process or the annealing process or both.

The released bio-compatible structure is suitable for incorporation into a biological environment, such as within an eye-mountable device or an implantable medical device, for example. Due to the encapsulating bio-compatible material, the surrounding environment is sealed from the embedded electronics. For example, if the structure is implanted in a biological host, or placed in an eye-mountable device to be exposed to tear fluid, the structure is able to be exposed to fluids of the biological host (e.g., tear fluid, blood, etc.), because the entire exterior surface is coated with bio-compatible material, except that the sensor electrodes 340 are exposed to allow detection of one or more analytes in the fluid.

The description in FIGS. 3A-3K describes one example of a process for fabricating a bio-compatible structure that can be embedded in an eye-mountable device. However, the process described with reference to FIGS. 3A-3K may be employed to create bio-compatible structures for other applications, such as other implantable electronic medical device applications. Such implantable electronic medical devices may include an antenna for communicating information (e.g., sensor results) and/or inductively harvesting energy (e.g., radio frequency radiation). Implantable electronic medical devices may also include electrochemical sensors or they may include other electronic devices. The process described with reference to FIGS. 3A-3K may be used to create bio-compatible structures suitable to be mounted on or in another part of the body. For example, bio-compatible structures may be mounted on or implanted under the skin, such as in the abdomen or the upper arm, on a tissue in the mouth, or in the brain to read electrical signals. The bio-compatible structure described above may be applied to any implantable device that detects bio-markers.

The bio-compatible structure may include electronics that are configured to perform functions in addition to, or as alternatives to, those described above. For example, the bio-compatible structure may include a light sensor, a temperature sensor, and/or other sensors useful for detecting diagnostically relevant information in an ophthalmic and/or implantable application. The electronics may, for example, obtain a temperature reading and then communicate the temperature information or use the temperature information to modify a measurement procedure with the electrochemical sensor. Moreover, the electronics may include a combination of capacitors, switches, etc., to regulate voltage levels and/or control connections with other electronics modules.

Figure 4A:
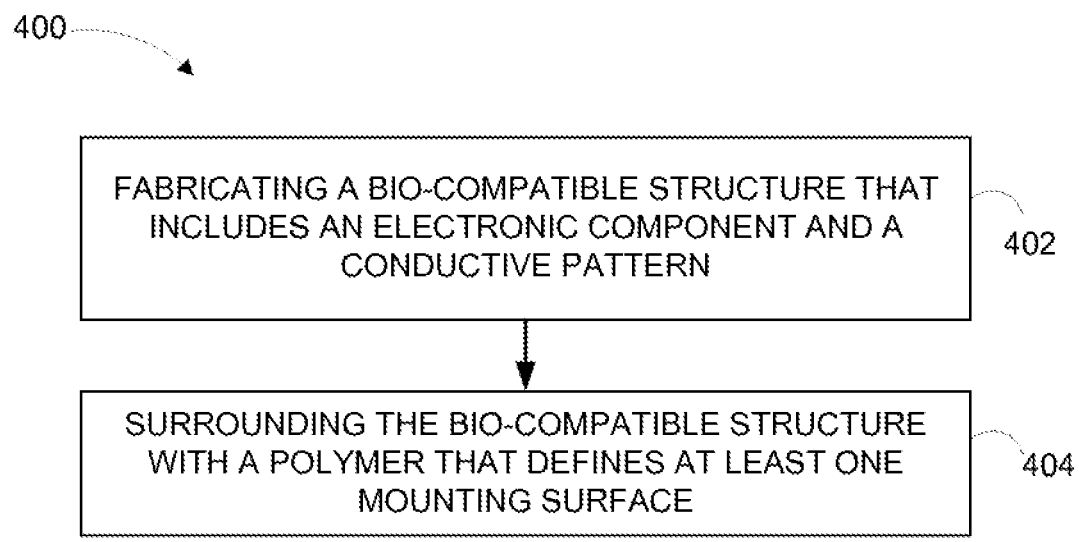
FIG. 4A is a flowchart of an example process for fabricating a mountable device.

FIG. 4A is a flowchart of an example method 400 for fabricating a mountable device. The mountable device could be an eye-mountable device, such as eye-mountable device 110 shown in FIG. 1 or eye-mountable device 210 shown in FIGS. 2A-2D.

The example method 400 involves fabricating a bio-compatible structure that includes an electronic component and a conductive pattern (block 402). The bio-compatible structure may be fabricated as described above with reference to FIGS. 3A-3K or described below with reference to FIG. 4B.

The method then includes surrounding the bio-compatible structure with a polymer that defines at least one mounting surface (block 404). For an eye-mountable device, the polymer could be a transparent polymer and may take the form of a disk or lens, as described with reference to FIGS. 2A-2D. Thus, the polymer could define a concave surface that is configured to be mounted to a corneal surface. In other examples, the polymer may define a surface configured to be mounted on the skin or on a tissue in the mouth. Other types of mounting surfaces are possible as well.

The bio-compatible structure could be surrounded by the polymer in various ways. In one example, a two-step injection molding process may be used. In the first step, a first layer of the polymer is formed in a mold, and the bio-compatible structure is placed on the first polymer layer. In the second step, a second layer of the polymer is formed in a mold so as to cover the bio-compatible structure on the first polymer layer. Other methods for surrounding the bio-compatible structure with polymer are possible as well.

Figure 4B:
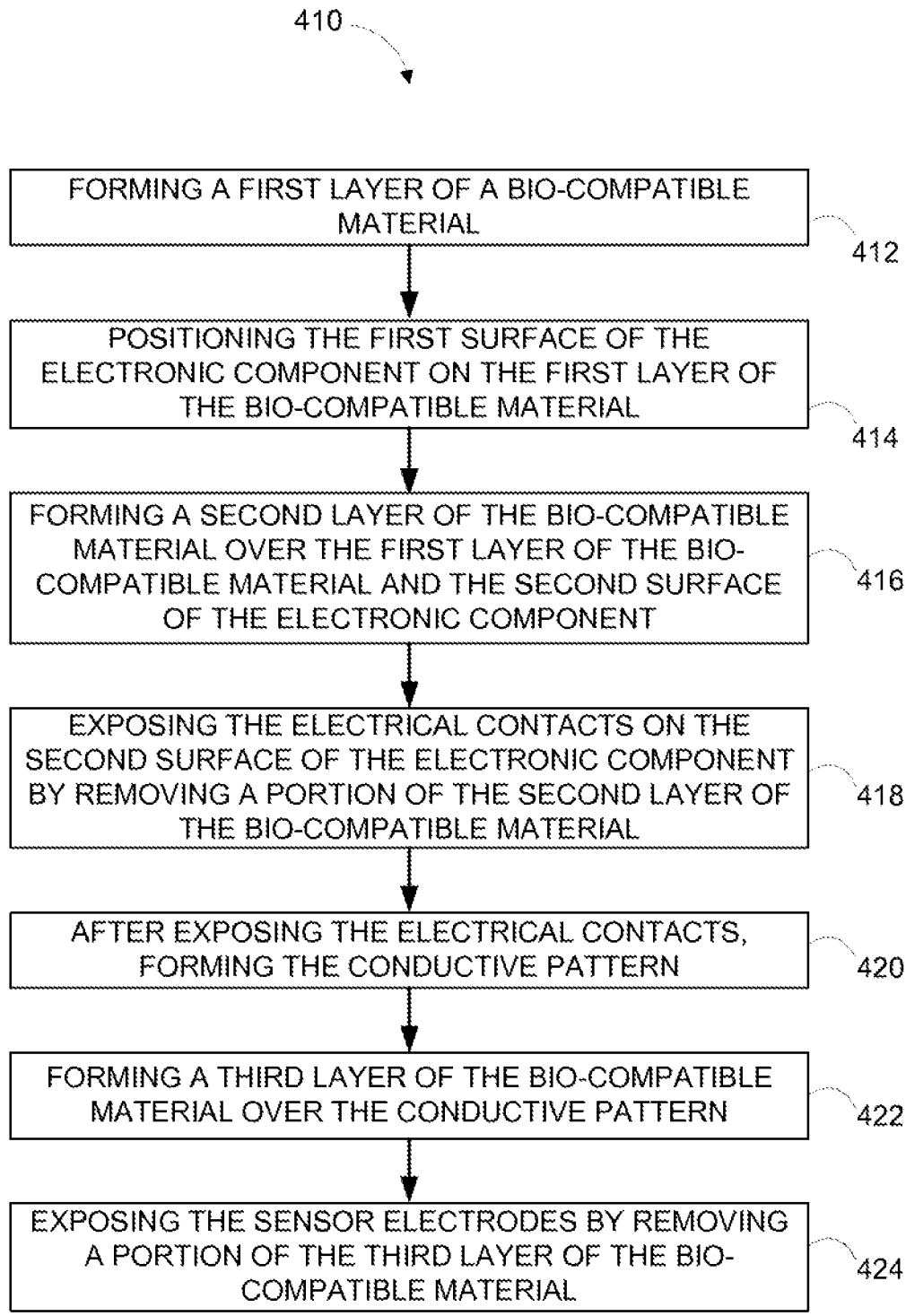
FIG. 4B is a flowchart of an example process for fabricating a bio-compatible structure.

FIG. 4B is a flowchart of an example method 410 for fabricating a bio-compatible structure. Once fabricated, the bio-compatible structure could be surrounded by a polymer that defines a mounting surface, as described above with reference to FIG. 4A. Alternatively, the bio-compatible structure could be used in an implantable device or used in other ways.

In the example method 410, the bio-compatible structure includes an electronic component and a conductive pattern. The electronic component could be an integrated circuit, a discrete component (such as a transistor, resistor, or capacitor), or some other type of electronic component. The electronic component may be the controller 150 described with reference to FIG. 1, for example. In this example, the electronic component has a first surface and a second surface opposite the first surface and includes one or more electrical contacts on the second surface, such as the chip 320 described with reference to FIGS. 3B-3K.

The example method 410 includes forming a first layer of a bio-compatible material (block 412). The first layer of the bio-compatible material may be the same as or similar to the first layer of bio-compatible material 310 as described with reference to FIGS. 3A-3K, for example. In one example embodiment, the first layer of bio-compatible material may be formed on a working substrate such as the working substrate 302 as described with reference to FIGS. 3A-3K.

The method 410 further includes positioning the first surface of the electronic component on the first layer of the bio-compatible material (block 414) and forming a second layer of the bio-compatible material over the first layer of the bio-compatible material and the second surface of the electronic component (block 416). The second layer of the bio-compatible material may be formed similarly to the second layer of bio-compatible material 330 as described with reference to FIGS. 3C-3K, for example.

The method 410 further includes exposing the electrical contacts on the second surface of the electronic component by removing a portion of the second layer of the bio-compatible material (block 418). Removing a portion of the second layer of the bio-compatible material may comprise applying a metal mask to certain portions of the structure, such as the metal mask 335 described with reference to FIGS. 3D-3E, and then subjecting the structure to a plasma to remove any exposed portions of the second layer.

The method 410 further includes, after exposing the electrical contacts, forming the conductive pattern (block 420). The conductive pattern defines at least sensor electrodes on the second layer of the bio-compatible material and electrical interconnects between the sensor electrodes and the electrical contacts on the electronic component. The conductive pattern may also define an antenna and electrical interconnects between the antenna and additional electrical contacts on the electronic component. The conductive pattern may define other types of interconnects, wires, or conductive structures as well.

The conductive pattern may be formed using any of the methods described herein. The sensor electrodes may be similar to the sensor electrodes 340, as described with reference to FIG. 3G. The electrical interconnects may be the same or similar to the interconnects 352 as described with reference to FIG. 3G. Additional components may also be positioned on the second polymer layer, such as the antenna 350 and the interconnects 354 described above with reference to FIG. 3G.

The method includes forming a third layer of the bio-compatible material over the conductive pattern (block 422). The third layer of the bio-compatible material may be similar to the layer of the bio-compatible material 360 described with reference to FIGS. 3H-3K.

The method 410 further includes exposing the sensor electrodes by removing a portion of the third layer of the bio-compatible material (block 426). The portion of the third layer may be removed by exposure of the portion to a plasma, such as described with reference to FIGS. 3J-3K.

Annealing processes may seal the three layers of bio-compatible material to fully encapsulate the bio-compatible structure, as described above.

Additionally, the assembled encapsulated structure may be etched to create a ring-shaped structure, via a metal mask and ensuing plasma application as described with reference to FIGS. 3I-3K. For example, the encapsulated structure may be etched to create a flattened-ring-shape similar to the ring-shaped sensing platform 230 shown and described in connection with FIGS. 2A-2D above. The encapsulated structure may also be etched in another shape, such as a rectangle, a circle (e.g., a disc), an oval, etc. to create a generally flat structure in which assembled electronics are encapsulated by sealed bio-compatible material.

The bio-compatible structure can then be embedded into polymeric material of a mountable device. Where the bio-compatible structure is given a flattened-ring shape, the structure can be embedded around the peripheral region of a generally circular polymeric material shaped to be contact-mounted to an eye, for example. Such a polymeric material may have, for example, a concave surface configured to be mounted over a corneal surface of an eye and a convex surface opposite the concave surface configured to be compatible with eyelid motion while mounted to the corneal surface. For example, a hydrogel material (or other polymeric material) can be formed around the bio-compatible structure in an injection molding process.

In other embodiments, the released encapsulated structure may be embedded into a mountable device to be mounted to another part of the body, such as the skin or in the mouth, for example. For example, bio-compatible structures may be mounted on or implanted under the skin, such as in the abdomen or the upper arm, on a tissue in the mouth, or in the brain to read electrical signals. The bio-compatible structure described above may be applied to any implantable device that detects bio-markers.

FIG. 5 depicts a computer-readable medium configured according to an example embodiment. In example embodiments, the example system can include one or more processors, one or more forms of memory, one or more input devices/interfaces, one or more output devices/interfaces, and machine-readable instructions that when executed by the one or more processors cause the system to carry out the various functions, tasks, capabilities, etc., described above.

In some embodiments, the disclosed techniques can be implemented by computer program instructions encoded on a non-transitory computer-readable storage media in a machine-readable format, or on other non-transitory media or articles of manufacture. FIG. 5 is a schematic illustrating a conceptual partial view of an example computer program product that includes a computer program for executing a computer process on a computing device, to perform any of the methods describe herein.

In one embodiment, the example computer program product 500 is provided using a signal bearing medium 502. The signal bearing medium 502 may include one or more programming instructions 504 that, when executed by one or more processors may provide functionality or portions of the functionality described above with respect to FIGS. 1-4B. In some examples, the signal bearing medium 502 can include a non-transitory computer-readable medium 506, such as, but not limited to, a hard disk drive, a Compact Disc (CD), a Digital Video Disk (DVD), a digital tape, memory, etc. In some implementations, the signal bearing medium 502 can be a computer recordable medium 508, such as, but not limited to, memory, read/write (R/W) CDs, R/W DVDs, etc. In some implementations, the signal bearing medium 502 can be a communications medium 510, such as, but not limited to, a digital and/or an analog communication medium (e.g., a fiber optic cable, a waveguide, a wired communications link, a wireless communication link, etc.). Thus, for example, the signal bearing medium 502 can be conveyed by a wireless form of the communications medium 510.

The one or more programming instructions 504 can be, for example, computer executable and/or logic implemented instructions. In some examples, a computing device is configured to provide various operations, functions, or actions in response to the programming instructions 504 conveyed to the computing device by one or more of the computer readable medium 506, the computer recordable medium 508, and/or the communications medium 510.

The non-transitory computer readable medium 506 can also be distributed among multiple data storage elements, which could be remotely located from each other. The computing device that executes some or all of the stored instructions can be a microfabrication controller, or another computing platform. Alternatively, the computing device that executes some or all of the stored instructions could be remotely located computer system, such as a server.

While various aspects and embodiments have been disclosed herein, other aspects and embodiments will be apparent to those skilled in the art. The various aspects and embodiments disclosed herein are for purposes of illustration and are not intended to be limiting, with the true scope being indicated by the following claims.

What is claimed is:

1. A method for fabricating a mountable device, the method comprising:
    fabricating a bio-compatible structure that includes an electronic component and a conductive pattern, wherein the electronic component has a first surface and a second surface opposite the first surface and includes electrical contacts on the second surface, wherein fabricating the bio-compatible structure comprises:
        forming a first layer of a bio-compatible material;
        positioning the first surface of the electronic component on the first layer of the bio-compatible material;
        forming a second layer of the bio-compatible material over the first layer of the bio-compatible material and the second surface of the electronic component;
        exposing the electrical contacts on the second surface of the electronic component by removing a portion of the second layer of the bio-compatible material;
        after exposing the electrical contacts, forming the conductive pattern, wherein the conductive pattern defines sensor electrodes on the second layer of the bio-compatible material and electrical interconnects between the sensor electrodes and the electrical contacts;
        forming a third layer of the bio-compatible material over the conductive pattern, wherein the third layer of the bio-compatible material includes a portion covering the sensor electrodes; and
        exposing the sensor electrodes by removing the portion of the third layer of the bio-compatible material covering the sensor electrodes; and
    surrounding the bio-compatible structure with a polymer, wherein the polymer defines at least one mounting surface of the mountable device.

2. The method of claim 1, wherein forming the first layer of the bio-compatible material comprises forming the first layer of the bio-compatible material on a working substrate.

3. The method of claim 2, wherein fabricating the bio-compatible structure further comprises:
    after exposing the sensor electrodes, releasing the first layer of the bio-compatible material from the working substrate.

4. The method of claim 1, wherein fabricating the bio-compatible structure further comprises:
    after exposing the sensor electrodes, annealing the first, second, and third layers of the bio-compatible material so that the layers are sealed together.

5. The method of claim 4, wherein the annealing fully encapsulates the bio-compatible structure with the bio-compatible material, except for the sensor electrodes.

6. The method of claim 1, wherein removing the portion of the second layer of the bio-compatible material comprises:
   forming a masking layer on the second layer of the bio-compatible material, wherein the masking layer exposes the portion of the second layer of the bio-compatible material;
   etching the portion of the second layer of the bio-compatible material exposed by the masking layer to provide a remaining portion of the second layer that is covered by the masking layer; and
   removing the masking layer from the remaining portion of the second layer.

7. The method of claim 6, wherein the remaining portion of the second layer of the bio-compatible material is substantially flush with the second surface of the electronic component.

8. The method of claim 1, wherein removing the portion of the third layer of the bio-compatible material covering the sensor electrodes comprises:
   forming a masking layer on the third layer of the bio-compatible material, wherein the masking layer exposes the portion of the third layer of the bio-compatible material;
   etching the portion of the third layer of the bio-compatible material exposed by the masking layer to provide a remaining portion of the third layer that is covered by the masking layer; and
   removing the masking layer from the remaining portion of the third layer.

9. The method of claim 8, wherein the remaining portion of the third layer of the bio-compatible material covers all of the conductive pattern except for the sensor electrodes.

10. The method of claim 1, wherein the sensor electrodes include a working electrode, a reference electrode, and a counter electrode of an electrochemical sensor.

11. The method of claim 10, wherein fabricating the bio-compatible structure further comprises:
   forming a reagent layer proximal to the sensor electrodes.

12. The method of claim 1, wherein the electronic component further includes additional electrical contacts on the second surface, and wherein the conductive pattern further defines an antenna on the second surface of the bio-compatible material and electrical interconnects between the antenna and the additional electrical contacts.

13. The method of claim 1, wherein the bio-compatible structure is ring shaped.

14. The method of claim 1, wherein the bio-compatible material comprises parylene.

15. The method of claim 1, wherein the mountable device is an eye-mountable device, and wherein the polymer defines a concave surface configured to mount the mountable device on a corneal surface and a convex surface configured to be compatible with eyelid movement when the concave surface is so mounted.

* * * * *